(12) United States Patent
Stride et al.

(10) Patent No.: US 11,007,495 B2
(45) Date of Patent: May 18, 2021

(54) METHOD AND APPARATUS FOR GENERATING BUBBLES

(71) Applicant: Oxford University Innovation Limited, Oxford (GB)

(72) Inventors: Eleanor Stride, Oxfordshire (GB);
Dario Carugo, Oxfordshire (GB);
Richard Browning, Oxfordshire (GB)

(73) Assignee: OXFORD UNIVERSITY INNOVATION LIMITED

( * ) Notice: Subject to any disclaimer, the term of this patent is extended or adjusted under 35 U.S.C. 154(b) by 270 days.

(21) Appl. No.: 16/071,699

(22) PCT Filed: Jan. 20, 2017

(86) PCT No.: PCT/GB2017/050144
§ 371 (c)(1),
(2) Date: Jul. 20, 2018

(87) PCT Pub. No.: WO2017/125753
PCT Pub. Date: Jul. 27, 2017

(65) Prior Publication Data
US 2019/0282973 A1    Sep. 19, 2019

(30) Foreign Application Priority Data

Jan. 20, 2016    (GB) ..................... 1601053

(51) Int. Cl.
*B01F 3/00*    (2006.01)
*B01F 3/04*    (2006.01)
*B01F 3/08*    (2006.01)
*B01F 5/04*    (2006.01)
(Continued)

(52) U.S. Cl.
CPC ........ *B01F 3/04978* (2013.01); *A61K 49/223* (2013.01); *A61K 49/226* (2013.01);
(Continued)

(58) Field of Classification Search
CPC ............. B01F 11/0266; B01F 3/04978; B01F 3/0446; B01F 3/0811; B01F 3/0819;
(Continued)

(56) References Cited

U.S. PATENT DOCUMENTS

2008/0319377 A1* 12/2008 Keenan ............... B01F 3/04106
604/24
2015/0125400 A1   5/2015 van Hoeve et al.
2015/0298157 A1* 10/2015 Weitz ..................... C12M 47/04
239/4

FOREIGN PATENT DOCUMENTS

CN    104801356 A    7/2015
EP    0680779 A1    11/1995
(Continued)

OTHER PUBLICATIONS

International Search Report for PCT/GB2017/050144 filed on Jan. 20, 2017, dated Apr. 7, 2017. 3 pages.
(Continued)

*Primary Examiner* — Anshu Bhatia
(74) *Attorney, Agent, or Firm* — Reising Ethington P.C.

(57) ABSTRACT

A method of generating bubbles of a first fluid in a second fluid, the method comprising: flowing a stream of the second fluid through a microfluidic channel; injecting a stream of the first fluid into the microfluidic channel through an aperture such that bubbles of the first fluid form in the second fluid; and sonicating the microfluidic channel with ultrasound so as to cause the bubbles formed at the aperture to divide.

15 Claims, 14 Drawing Sheets

(51) Int. Cl.
*B01F 11/02* (2006.01)
*B01F 13/00* (2006.01)
*A61K 49/22* (2006.01)

(52) U.S. Cl.
CPC .......... *B01F 3/0446* (2013.01); *B01F 3/0811* (2013.01); *B01F 3/0819* (2013.01); *B01F 5/0473* (2013.01); *B01F 11/0241* (2013.01); *B01F 11/0266* (2013.01); *B01F 13/0059* (2013.01); *B01F 2003/0849* (2013.01); *B01F 2215/0032* (2013.01); *B01F 2215/0431* (2013.01); *B01F 2215/0454* (2013.01)

(58) Field of Classification Search
CPC ................ B01F 5/0473; B01F 11/0241; B01F 13/0059; B01F 2003/0849; B01F 2215/0032; B01F 2215/0431; B01F 2215/0454; A61K 49/223; A61K 49/226
See application file for complete search history.

(56) References Cited

FOREIGN PATENT DOCUMENTS

| WO | 2011025893 A1 | 3/2011 |
| WO | 2013184075 A1 | 12/2013 |
| WO | 2014066624 A1 | 5/2014 |

OTHER PUBLICATIONS

Castro-Hernandez, Elena, et al. Microbubble generation in a co-flow operated new regime. The Royal Society of Chemistry 2011, Lab Chip, 2011, 2023-2029.

Chen, Chuanpin, et al. Production of monodispersed micron-sized bubbles at high rates in a microfluidic device. Applied Physics Letters 95, 144101 (American Institute of Physics, 2009).

Chen, Haosheng, et al. Sonication-Microfluidics for Fabrication of Nanoparticle-Stabilized Microbubbles. American Chemical Society 2014, Langmuir, 2014, 30, 4262-4266.

Hettiarachchi, Kanaka, et al. On-chip generation of microbubbles as a practical technology for manufacturing contrast agents for ultrasonic imaging. The Royal Society of Chemistry 2007, Lab Chip, 2007, 7, 463-468.

Peyman, Sally A., et al. Expanding 3D geometry for enhanced on-chip microbubble production and single step formation of liposome modified microbubbles. The Royal Society of Chemistry 2012, Lab Chip, 2012, 12, 4544-4552.

Sennoga, Charles A., et al. On Sizing and Counting of Microbubbles Using Optical Miscroscopy. Ultrasound in Med. & Biol., vol. 36, No. 12, pp. 2093-2096, 2010.

\* cited by examiner

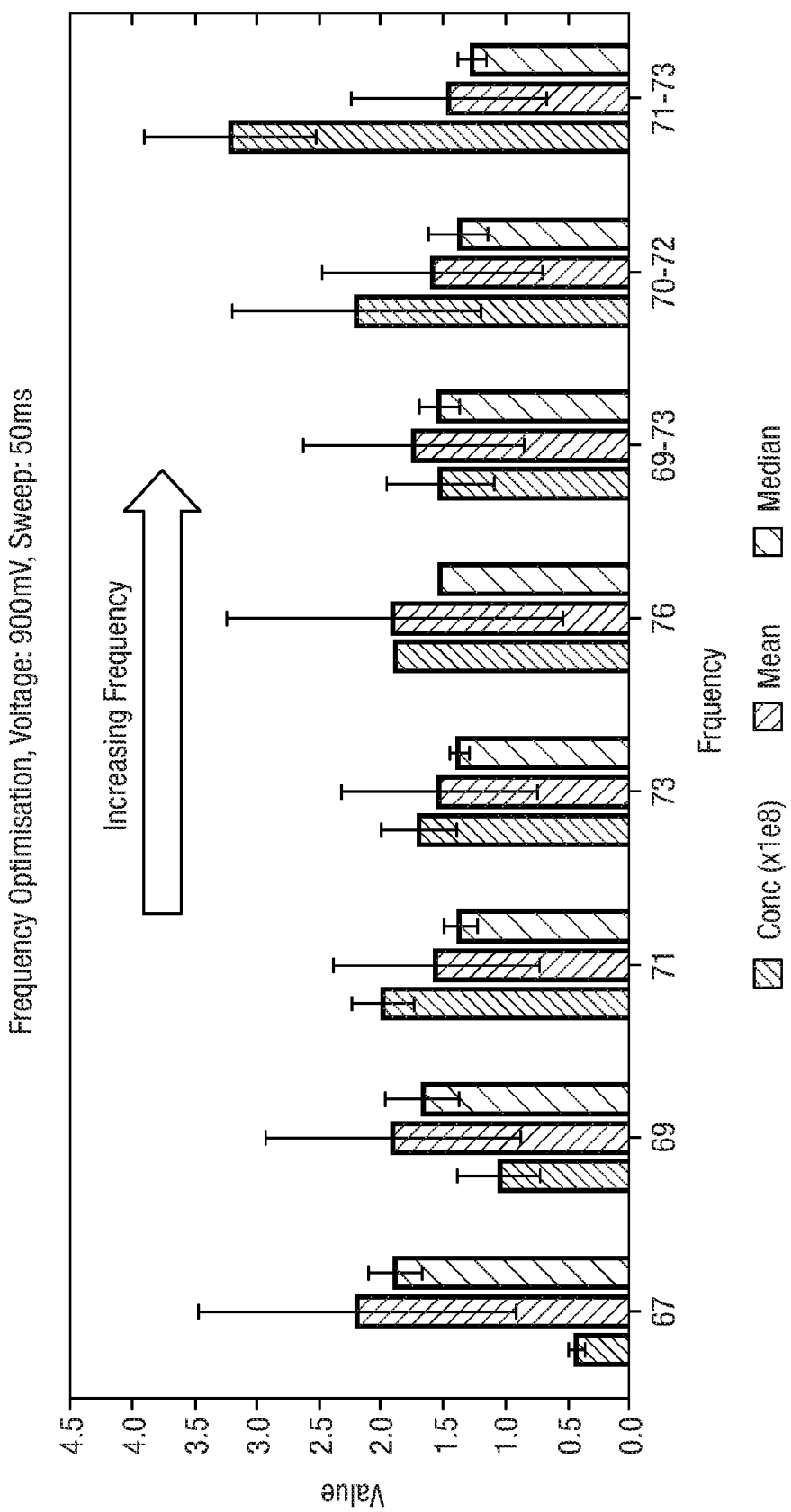

Fig. 8a
11 kPa
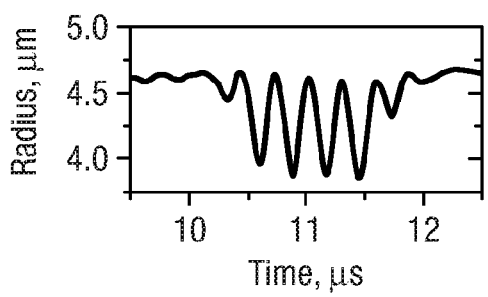 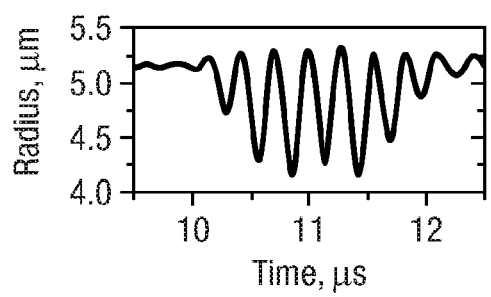
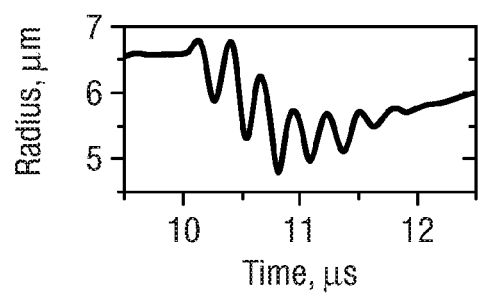 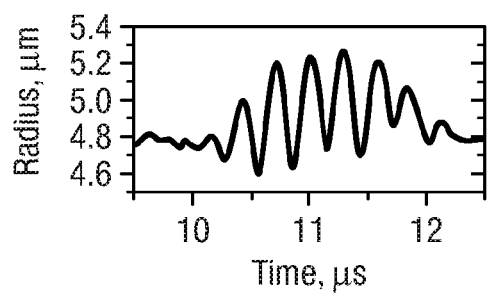
Fig. 8b
115 kPa
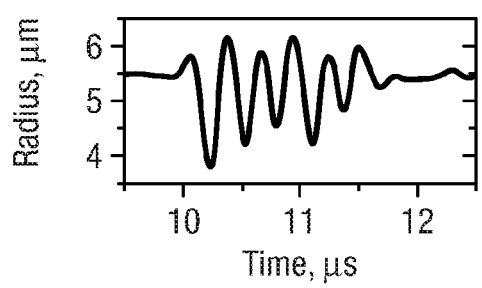 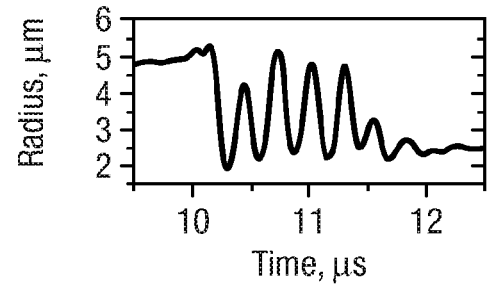
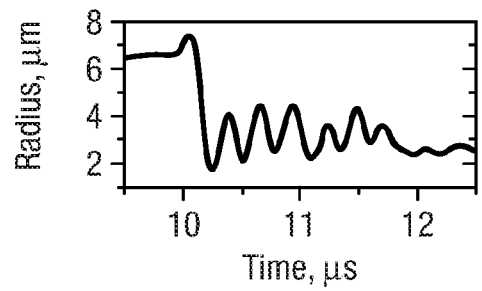 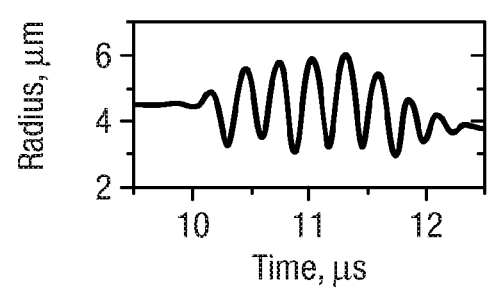

METHOD AND APPARATUS FOR GENERATING BUBBLES

CROSS-REFERENCE TO RELATED APPLICATIONS

This is a United States national phase patent application claiming the benefit of priority from Patent Cooperation Treaty patent application PCT/GB2017/050144 filed on Jan. 20, 2017, which claims the benefit of priority from GB patent application number GB 1601053.0 filed on Jan. 20, 2016, the entire contents of which are incorporated herein.

TECHNICAL FIELD

The invention relates to a method and apparatus for generating bubbles. In particular, the invention relates to microbubbles.

BACKGROUND ART

Microbubbles (micron-scale bubbles—bubbles of a fluid having a diameter less than 1 mm) have many applications, particularly in the field of medicine.

For example, gas-filled microbubbles stabilised by a phospholipid or polymer coating are routinely used in medical imaging as ultrasound contrast agents, being capable of enhancing ultrasound backscatter from blood by several orders of magnitude. The microbubble usually comprises a core of a high molecular weight gas (i.e., perfluorocarbon or sulphur hexafluoride) to enhance sample stability both in vivo and during handling or storage. In clinical formulations, the outer coating usually comprises saturated phospholipids or denatured albumin. Moreover, the microbubble coating can be employed as a scaffold for transporting biologically active compounds or targeting agents in the haematic circulation, which has opened the way for the use of microbubble as a vehicle in therapeutic applications such as drug delivery or gene therapy.

The acoustic response and therefore the clinical utility of microbubbles are profoundly influenced by their physical characteristics, including size, size distribution, and mechanical/rheological properties of the coating layer. These have been observed to depend on the chemical formulation of the microbubble coating and on the production technique.

Various methods and apparatuses for generating microbubbles are known. Methods developed for batch production of microbubbles include sonication, high shear emulsification, membrane emulsification, and coaxial electro-hydrodynamic atomisation.

Bulk sonication is the most commonly employed method in both academic and industrial laboratories, and involves dispersing gas or liquid in a suspension of a coating material using high intensity ultrasound. The size distribution of microbubbles obtained from bulk sonication is however relatively broad, which makes it necessary to perform additional, time-consuming post-production procedures (i.e., fractionation or filtration) in order to remove any large bubbles which could cause vascular occlusion after intravenous injection. Furthermore, the lack of process automation makes this technique highly operator dependent and difficult to reproduce faithfully over multiple iterations. WO-2011/025893 discloses an example of using bulk sonication to produce microbubbles.

More recently, microfluidic-based techniques have been proposed as an alternative to batch methods for producing relatively monodisperse microbubbles. A typical microfluidic device consists of a cross-flow (i.e., flow focusing) or T-junction architecture, in which gas and fluid streams are forced to flow into a confined microenvironment where break-up of the gas stream into individual microbubbles occurs. Depending on the geometrical properties of the microenvironment and the fluid dynamic field, different microbubble production regimes have been demonstrated. However, the narrower size distribution is frequently accompanied by low production rates, the need for chemical additives to adjust fluid viscosity and surface tension, and in some cases lower microbubble stability. These factors have hindered the adoption of microfluidics as a viable technology for industrial production of microbubbles for clinical usage. US-2015/0125400 discloses an example using a microfluidic based technique to produce microbubbles.

The present invention has been developed to at least partly address some of the problems discussed above.

SUMMARY OF THE INVENTION

According to a first aspect of the invention there is provided a method of generating bubbles of a first fluid in a second fluid, the method comprising: flowing a stream of the second fluid through a microfluidic channel; injecting a stream of the first fluid into the microfluidic channel through an aperture such that bubbles of the first fluid form in the second fluid; and sonicating the microfluidic channel with ultrasound so as to cause the bubbles formed at the aperture to divide.

According to a second aspect of the invention there is provided an apparatus for generating bubbles of a first fluid dispersed in a second fluid, the apparatus comprising: a microfluidic channel configured to provide a flow path for the second fluid; an aperture in the microfluidic channel configured to allow injection of a stream of the first fluid into the microfluidic channel such that bubbles of the first fluid form in the second fluid; and an ultrasound source configured to sonicate the microfluidic channel with ultrasound so as to cause the bubbles to divide.

Thus, according to the invention, formation of bubbles at an aperture in a microfluidic channel is applied in combination with sonication of the microfluidic channel with ultrasound to divide the bubbles formed at the aperture. This allows for formation of bubbles with several advantages over the known methods described above. Embodiments of may provide one or more of the following advantages:

Continuous-flow production of bubbles at concentration, composition and mean size comparable to those of clinical formulations.

Bubble production without exogenous cavitation nuclei or in some cases without surfactant additives, making the method suitable for producing a large range of different microbubble formulations of clinical relevance.

Direct bubble production (i.e., no need for additional post-production steps).

Possibility of tuning the physical properties of the microenvironment (including both hydrodynamic and acoustic fields) to obtain desired bubble properties, with higher control compared to batch sonication, providing the potential for improved reproducibility between experiments and narrower bubble size distributions.

Ease of operation, resulting in increased throughput and relatively fast production rates.

Large microfluidic channels compared to known microfluidic methods, resulting in faster priming, higher operating flow rates, and reduced likelihood of channel clogging, the latter resulting in a significant increase in apparatus lifetime, and therefore reduced cost.

Fabrication of the apparatus using a low-cost and facile replica moulding technique, which makes it attractive for a wide range of laboratory settings.

BRIEF DESCRIPTION OF THE DRAWINGS

Embodiments of the invention will be now described below by way of example and with reference to the drawings, in which:

FIG. 7 is a graph showing the dependence of bubble size and concentration on the sonication frequency for the exemplary apparatus;

FIG. 8 shows examples of microfluidic bubble radial responses upon ultrasound exposure at 3.5 MHz, pulse length of 5 cycles and peak negative pressures of a) 11 kPa and b) 115 kPa;

DETAILED DESCRIPTION

Figure 1:
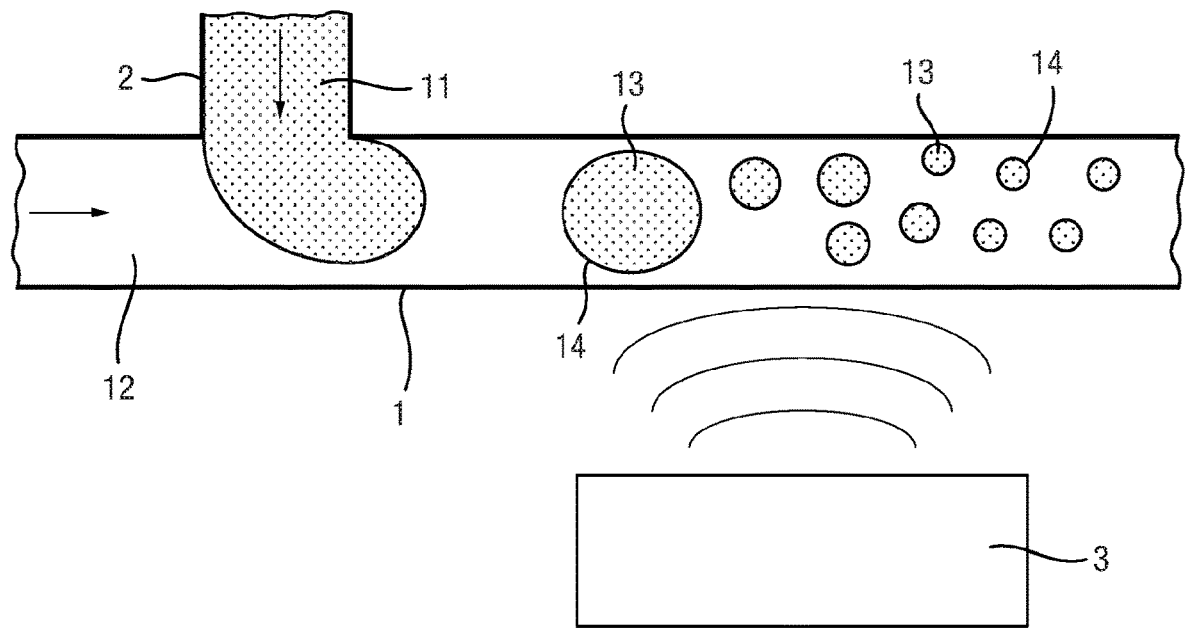
FIG. 1 schematically shows an apparatus according to an embodiment of the invention.
Figure 2:
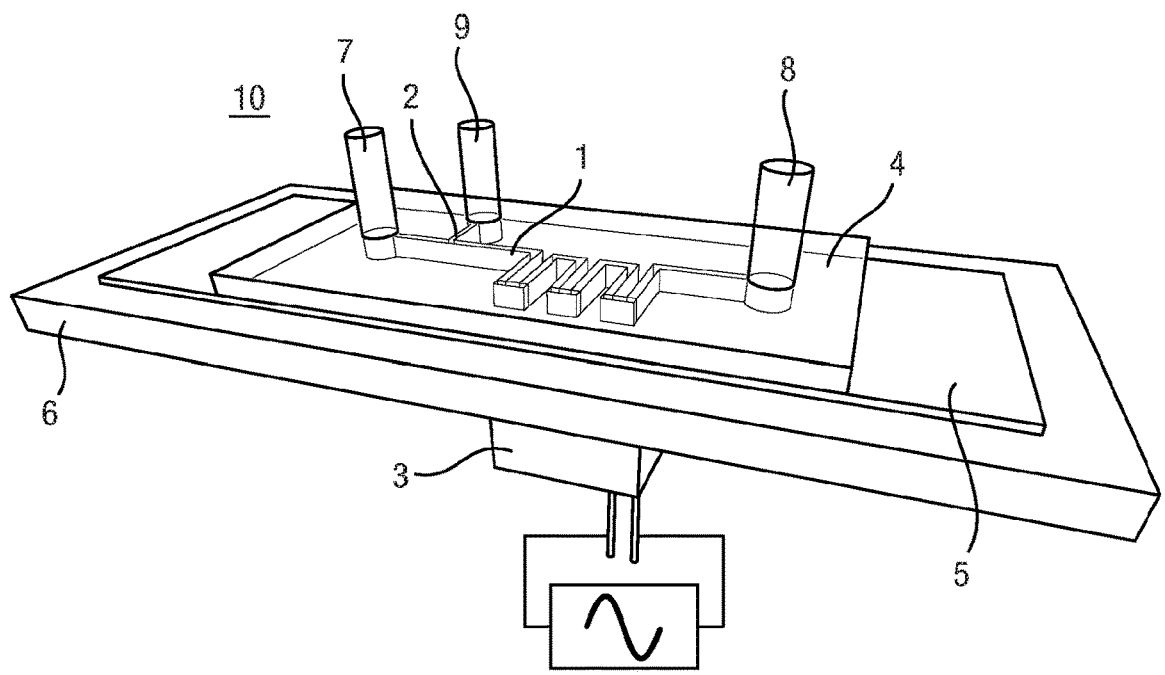
FIG. 2 schematically shows an exemplary apparatus of the invention.
Figure 3:
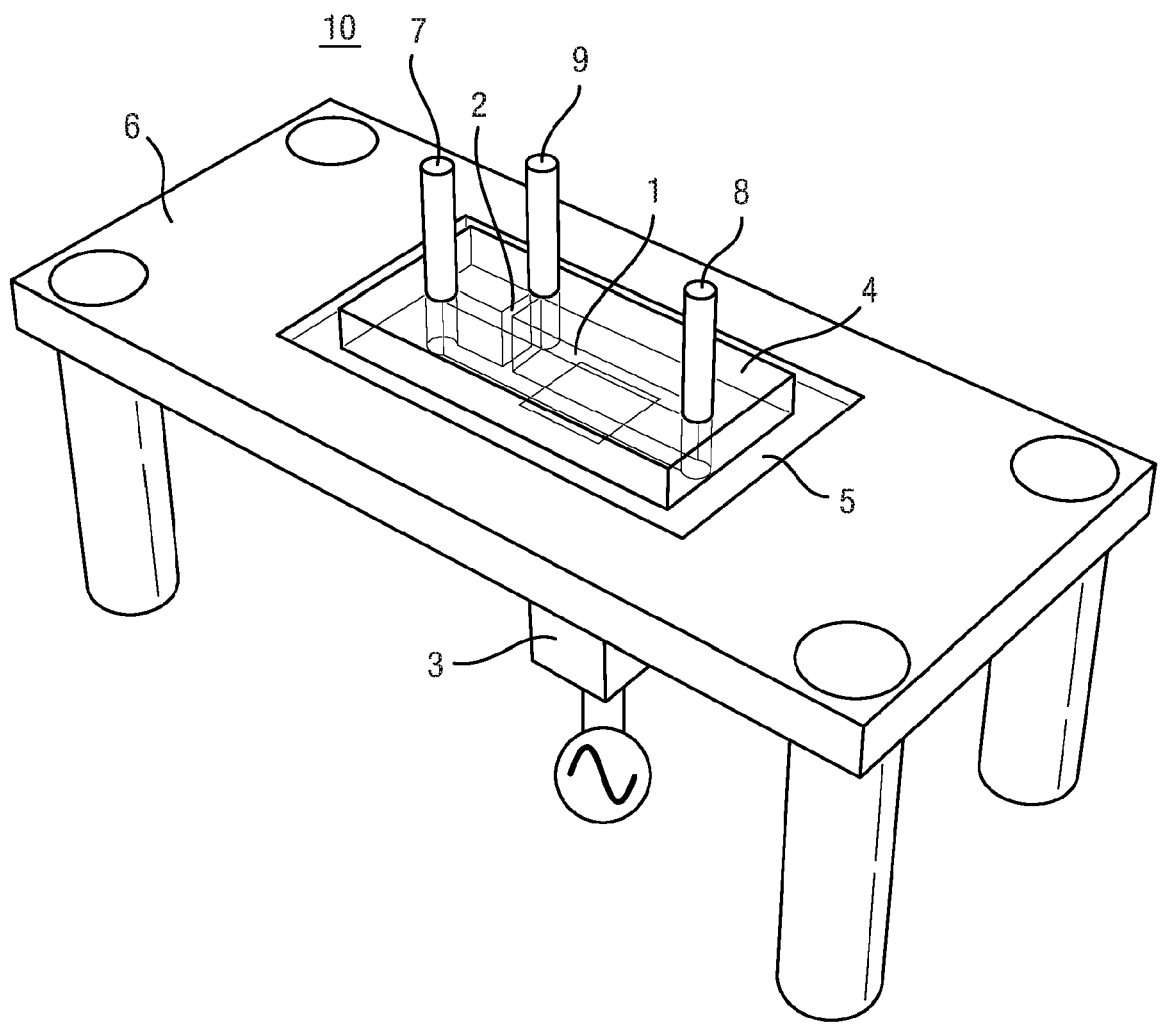
FIG. 3 schematically shows another exemplary apparatus of the invention.
Figure 4A:
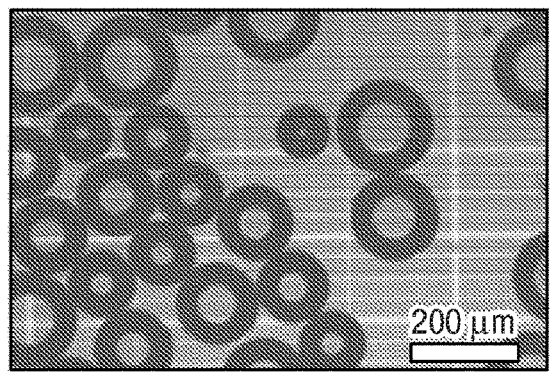
FIGS. 4A and 4B show microscope images of bubbles.
Figure 4B:
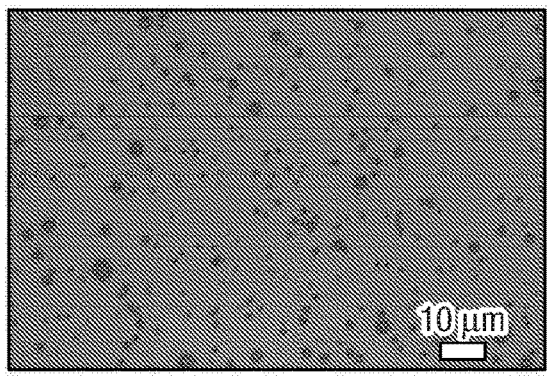

FIG. 1 is a schematic diagram showing an apparatus 10 for generating bubbles 13 (e.g. microbubbles) of a first fluid 11 dispersed in a second fluid 12, the apparatus 10 comprising a microfluidic channel 1 configured to provide a flow path for the second fluid 12 introduced through an inlet 9. An aperture 2 is provided in the microfluidic channel 1 configured to allow injection of a stream of the first fluid 11, introduced into the apparatus 10 through an inlet 7, into the microfluidic channel 1 such that bubbles 13 of the first fluid 11 form in the second fluid 12. The apparatus 10 also includes an ultrasound source 3 configured to sonicate the microfluidic channel 1 with ultrasound so as to cause the bubbles 13 to divide. Exemplary apparatuses according to the invention are shown in FIG. 2 and FIG. 3.

The apparatus 10 is relatively simple and hence may be manufactured in a straightforward manner and at low cost, for example using replica moulding techniques.

Bubbles 13 are generated by flowing a stream of the second fluid 12 through the microfluidic channel 1, injecting a stream of the first fluid 11 into the microfluidic channel 1 through the aperture 2 such that bubbles 13 of the first fluid 11 form in the second fluid 12 and sonicating the microfluidic channel 1 with ultrasound so as to cause the bubbles 13 formed at the aperture 2 to divide.

The ultrasound may have a frequency corresponding to a resonance of the microfluidic channel. The impedance and/or phase angle of an ultrasound source sonicating the microfluidic channel may be measured using any suitable technique. The frequency corresponding to a resonance of the microfluidic channel is determined based on the measured impedance and/or phase angle.

The term bubbles herein refers generally to volumes of a first fluid in a second fluid. The term microfluidic herein refers to systems having micron-scale (or lower) dimensions e.g. channels having a hydraulic diameter on a micron-scale (e.g. less than 1 mm).

The bubbles 13 may form at the aperture 2 when the stream of the first fluid 11 meets the stream of the second fluid 12. The bubbles thus formed may flow through the microfluidic channel in a flow direction due to a positive pressure gradient generated by the stream of the second fluid 12 and/or the stream of the first fluid 11.

The microfluidic channel 1 is sonicated with ultrasound so as to cause the bubbles 13 formed at the aperture to divide. Ultrasound from the ultrasound source 3 may be transmitted through the walls of the microfluidic channel 1, the second fluid 12, and/or the bubbles 13 of the first fluid 11. The ultrasound causes the bubbles 13 to divide. The division of the bubbles is thought to be attributed to volumetric oscillation of the bubbles 13 within the microfluidic channel when exposed to ultrasound and/or vibrational motion of the interface between the bubbles 13 and the second fluid 12 induced by the ultrasound.

The apparatus 10 may be operated continuously, thereby providing continuous-flow production of the bubbles 13 in a straightforward manner, at relatively high throughput and without the need for additional post-production steps. The bubbles 13 may be formed without exogenous cavitation nuclei. The physical properties of the apparatus 10, including both hydrodynamic and acoustic fields, may be tuned to obtain desired bubble properties. Higher control of the bubble properties may be achieved than with batch sonication, providing the potential for improved reproducibility between experiments and narrower bubble size distributions. Some examples of how the properties of the apparatus 10 may be varied are given below.

The sonication may be applied to the microfluidic channel 1 at a location adjacent to the aperture 2. The length of the microchannel 1 between the aperture 2 and the location at which the sonication is applied may preferably be no more than a first predefined length. Preferably, the first predefined length may be no more than 25 mm. Optionally, the first predefined length may be no more than 10 mm. Optionally, the first predefined length may be no more than 5 mm.

The stability of relatively large bubbles 13 formed at the aperture 2 may decrease with distance from the aperture 2, therefore, the first predefined length may affect the stability of bubbles generated by the invention. For example, if the first predefined length is too long, the bubbles formed at the aperture may coalesce before they are sonicated which may reduce the production rate of the bubbles but if the first predefined length is too short, the sonication may reduce the monodispersity of the bubbles formed at the aperture.

The hydraulic diameter of the microfluidic channel 1 may affect the size distribution and/or stability of bubbles generated by the invention. The hydraulic diameter, DH, is defined in the conventional way, i.e. by the formula below in which A is the transverse cross-sectional area of the microfluidic channel 1 and P is the wetted perimeter of the transverse cross-section of the microfluidic channel 1. For a completely full channel the wetted perimeter is equal to the perimeter.

$$D_H = \frac{4A}{P}$$

If the hydraulic diameter of the microfluidic channel 1 is too small the bubbles may not be stable or there may be a risk of clogging, but if the hydraulic diameter of the microfluidic channel 1 is too large, the bubbles produced might be too large to be useful.

The microfluidic channel 1 preferably has a hydraulic diameter of at most 1 mm.

Optionally the microfluidic channel 1 may have a hydraulic diameter of at most 500 μm or at most 250 μm.

Optionally the microfluidic channel 1 may have a hydraulic diameter of at least 50 at least 80 μm (e.g. 83.5 μm), at least 100 or at least 150 The hydraulic diameter of the microfluidic channel 1 may be larger than is typically used in known microfluidic bubble-production techniques, with the result that the apparatus 10 may be primed faster, may be operated with higher flow rates and may have less likelihood of clogging, thereby increasing lifetime and reducing overall cost.

The microfluidic channel 1 may have a transverse cross-section that is circular, rectangular or square in shape. The transverse cross-section of the microfluidic channel 1 may be substantially the same for the entire length of the microfluidic channel 1. For a rectangular cross-section the microfluidic channel 1 may have a width of at most 500 μm or at most 250 and/or a width of at least 50 at least 100 or at least 150 The microfluidic channel 1 may have a height of at most 500 μm or at most 250 and/or a height of at least 50 at least 100 or at least 150 μm.

The ultrasound may divide the bubbles 13 continuously as they flow through the portion of the microfluidic channel 1 to which sonication is applied. The sonication may be applied to a length of the microfluidic channel 1 that is at least a second predefined length. Preferably, the second predefined length may be at least 2 mm. Optionally, the second predefined length may be at least 5 mm. Optionally, the second predefined length may be at least 10 mm. Preferably the second predefined length may be at most 100 mm. Optionally, the second predefined length may be at most 50 mm, or at most 25 mm.

The microfluidic channel 1 may be linear, as shown in FIG. 3. In order to condense the apparatus 10, the microfluidic channel 1 may include a non-linear section, as shown in FIG. 2. The non-linear section may have a serpentine, or zig-zag, arrangement, for example. The second predefined length may affect the size distribution of bubbles generated by the invention. If the second predefined length is too short, the size distribution may become too broad, but if the second predefined length is too long, bubbles may destabilise reducing the production rate.

The microfluidic channel 1 may be connected at one end to a first inlet 7 for providing the stream of the second fluid 12 to the microfluidic channel 1. The first inlet 7 may be connected to a pumping means e.g. a syringe pump to provide constant volumetric fluid flow or a pressure controlled pump to provide flow at a constant pressure. The opposite end of the microfluidic channel 1 may be connected to an outlet 8 for outputting bubbles 13 of the first fluid 11 in the second fluid 12. The hydraulic diameter of the first inlet 7 and the outlet 8 may be larger than that of the microfluidic channel 1.

The aperture 2 preferably has a hydraulic diameter of at most 1 mm. Optionally the microfluidic channel 1 may have a hydraulic diameter of at most 500 μm or at most 250 μm. Optionally the microfluidic channel 1 may have a hydraulic diameter of at least 50 μm, at least 70 μm (e.g. 71 μm), at least 100 μm or at least 150 μm.

The cross-section of the aperture 2 may be the same as the cross-section of the microfluidic channel 1. The cross-section of the aperture may be smaller than the cross-section of the microfluidic channel 1. The hydraulic diameter of the aperture may affect the size distribution and/or stability of bubbles generated by the invention. If the hydraulic diameter of the aperture 2 is too small, the size of bubbles generated at the aperture may be less affected by the ultrasound, but if the hydraulic diameter of the microfluidic channel is too large, the first fluid 11 may not form bubbles at the aperture at all.

The aperture 2 may be connected to a second inlet 9 for providing the stream of the first fluid 11. The second inlet 9 may be connected to a pumping means e.g. a syringe pump to provide constant volumetric fluid flow or a pressure controlled pump to provide flow at a constant pressure. The hydraulic diameter of the second inlet 9 may be larger than that of the microfluidic channel 1.

The microfluidic channel 1 (and optionally at least part of the first and second inlets 7, 9 and the outlet 8) may be formed in a substrate 4 made from, for example, silicon, glass or a polymer. The polymer may be selected from, for example, polystyrene, polyvinyl chloride, polymethyl methacrylate, cyclic olefin copolymer, polycarbonate, and polydimethylsiloxane (PDMS). The substrate 4 may be fixed to a supporting layer 5 for supporting the substrate 4. The supporting layer 5 may be formed from for example, silicon, glass or a polymer. The polymer may be selected from, for example, polystyrene, polyvinyl chloride, polymethyl methacrylate, cyclic olefin copolymer, polycarbonate, and polydimethylsiloxane. The thickness of the supporting layer may be selected to minimise attenuation of ultrasound waves.

The frequency of ultrasound applied to the microfluidic channel 1 preferably has frequency of at least 20 kHz. Optionally the frequency may be at least 50 kHz, or at least 70 kHz. Preferably the frequency is at most 250 kHz, or at most 100 kHz. Optionally the frequency may be most 75 kHz. Optionally, the frequency may be in a range of from 71 kHz to 73 kHz.

Frequency sweeping may be used in which the ultrasound frequency is varied (e.g. scanned) within a range of frequencies (e.g. a range of from 71 kHz to 73 kHz). The frequency of the ultrasound may affect the size distribution and production rate of bubbles generated by the invention. If the frequency of the ultrasound is too low the mean bubble size may be too large and the production rate too low, if the frequency is too high, the mean bubble size may also be too high due to failure in causing the bubbles to divide.

The ultrasound may have a frequency corresponding to a resonance of the microfluidic channel, e.g. a resonant frequency of the microfluidic channel. This improves the efficiency of the transfer of acoustic energy to the device.

The impedance and/or phase angle of an ultrasound source sonicating the microfluidic channel may be measured, wherein the frequency corresponding to a resonance of the microfluidic channel is determined based on the measured impedance and/or phase angle.

The impedance and/or phase angle (of, e.g. an ultrasound transducer) may be measured for a number of different frequencies of sonication of the microfluidic channel. The frequency corresponding to a resonance of the microfluidic channel may be determined based on a frequency that corresponds to a peak minimum impedance (see FIG. 19) and/or a peak maximum phase angle (see FIG. 20). For example, the frequency corresponding to a resonance of the microfluidic channel may be set as the frequency of peak minimum impedance or the frequency of peak maximum phase angle, or an average of these frequencies.

The ultrasound may be configured to generate peak negative pressures in the first and second fluids 11, 12 flowing though the microfluidic channel 1 of at least 10 kPa. Optionally the ultrasound may be configured to generate peak negative pressures in the microfluidic channel of at least 50 kPa, at least 100 kPa, at least 500 kPa, or at least 1 MPa. The amplitude of the ultrasound may affect the size distribution of bubbles generated by the invention. For example, if the amplitude is too low, the mean bubble size may be too large, but if the amplitude is too high, the size distribution of the bubbles may be too broad.

The ultrasound source 3 may be a piezoelectric transducer. The piezoelectric transducer may be driven (e.g. by a 55 dB power amplifier) driven by a voltage selected according to the transducer transfer function to achieve the desired in-channel pressure, for example, up to 2 MPa. A conventional transducer may be driven at a voltage of at least 300 mV, at least 500 mV or at least 900 mV, or may be driven at a voltage of no more than 1000 mV, no more than 1200 mV or no more than 1500 mV. The transducer may be driven at frequency corresponding to a resonance of the microfluidic channel, as described above.

The ultrasound source 3 may be coupled to the substrate 4 or supporting layer 5 directly or indirectly. For example, the ultrasound source 3 may be coupled to the substrate 4 or supporting layer 5 indirectly via a layer of ultrasound transmitting fluid, such as glycerol or an ultrasound gel.

The ultrasound source 3 may be fixed to a base plate 6. The based plate 6 may be configured to allow selective attachment/detachment of the substrate 4 and/or supporting layer 5. The undivided bubbles 13 formed at the aperture 2 may have an average diameter of at least 50 µm, at least 100 µm, at least 150 µm, or at least 200 µm. The divided bubbles after sonication have an average diameter of at most 10 µm, at most 5 µm, or at most 2 µm.

The ratio of the hydraulic diameter of the microfluidic channel 1 and the average diameter of bubbles 13 formed at the aperture 2, may be at most 10. Optionally, the ratio of the hydraulic diameter of the microfluidic channel 1 and the average diameter of bubbles 13 formed at the aperture 2 may be at most 5 or at most 2. The ratio of the hydraulic diameter of the microfluidic channel 1 and the average diameter of divided bubbles 13 after sonication, may be at least 10. Optionally, the ratio of the hydraulic diameter of the microfluidic channel 1 and the average diameter of divided bubbles 13 after sonication, may be at least 50, at least 100, at least 250 or at least 500.

The diameters of the divided bubbles after sonication may have a coefficient of variation (the standard deviation divided by the mean diameter) of less than 60%, less than 50% or less than 40%.

The first fluid 11 and the second fluid 12 may be immiscible. The second fluid 12 may be a liquid or a gas. The first fluid 11 may be a liquid or a gas. In one example, the second fluid 12 is a liquid and the first fluid 11 is a gas. In another example, the second fluid 12 is a liquid and the first fluid 11 is a liquid.

Where the first fluid 11 or second fluid 12 is a liquid, it may be for example an aqueous solution or an oil. Where the first fluid 11 and second fluid 12 are liquids, they may both be aqueous solutions, or one may be an aqueous solution and the other may be an oil.

Where the first fluid 11 or second fluid 12 is a gas, it may be for example oxygen, nitrogen, perfluorocarbon or sulphur hexafluoride.

The first fluid may be injected into the microfluidic channel 1 in the presence of a surfactant 14 such that the bubbles 13 formed at the aperture 2 comprise a surfactant 14 at an interface with the second fluid 12.

The surfactant 14 may be provided in the same stream as the second fluid 12, e.g. as a solute or emulsion in the second fluid 12, or may optionally be introduced in a separate stream, e.g. through a further inlet. The surfactant 14 may comprise one or more of a phospholipid, a protein (e.g. albumin) or a polymer.

The surfactant 14 may help stabilise the bubbles 13. If the first and second fluids 11, 12 are miscible, a surfactant 14 may be required. If the first and second fluids 11, 12 are immiscible the surfactant 14 may not be required for bubbles 13 to be formed, but may optionally be provided to improve the stability of the bubbles 13.

The surfactant 14 and/or the first fluid 11 may comprise a pharmaceutical product e.g. a biologically or pharmacologically active agent or drug.

The first fluid 11 may comprise a gas with therapeutic properties e.g. to treat hypoxia and/or enable the bubbles to be used as contrast agents for ultrasound imaging.

Bubbles generated in accordance with the invention may have a wide range of applications, which are often biomedical applications. Applications of the bubbles include, without limitation: one or more of an ultrasound contrast agent, drug delivery, gene therapy, a means of transporting biologically active compounds, targeting agents in the haematic circulation, foams in food or cosmetics, particulate scavenging, or density modulation in materials processing. The method can be applied to produce nano- or micro-particulate systems, and particularly in those production processes which may benefit from the physical effects of an acoustic field. These may include, but are not limited to, the production of liposomes, polymerosomes, niosomes, and polymeric micelles.

FIG. 2 and FIG. 3. show exemplary apparatuses 10 according to the invention. In the apparatuses 10, a microfluidic channel 1, first inlet 7, outlet 8 and second inlet 9 were formed in a 5 mm thick PDMS substrate. The microfluidic channel had a rectangular cross-section with a height of 50 μm and a width of 250 μm. The PDMS substrate was bonded to a 170 μm thick glass supporting layer 5. The microfluidic channel 1 of the apparatus shown in FIG. 2 included a nonlinear, serpentine section downstream of the aperture 2. The microfluidic channel 1 of the apparatus shown in FIG. 3 was linear.

Experiments were performed using the apparatus 10 shown in FIG. 3 as follows:

A 19.1 mm thick piezoelectric transducer, as an ultrasound source 3, was coupled to the glass supporting layer 5 via a layer of glycerol. A base plate 6 was provided for supporting the glass supporting layer 5 and the substrate 4.

A phospholipid solution was input via the first inlet 7 to provide a stream of the second fluid 12 and a surfactant to the microfluidic channel 1. Syringe pumps (World Precision Instruments Inc., Florida, USA) were employed to control the fluid flow through the microfluidic channel. The second fluid 12 corresponded to a suspension of 1,2-Distearoyl-sn-glycero-3-phosphocholine (DSPC, from Avanti Polar Lipids, Alabama, USA) and polyoxyethylene (40) stearate (PEG40, from Sigma Aldrich, Gillingham, UK), at a molar ratio of 9:1, in phosphate buffered saline (PBS, from Thermo Fisher Scientific Inc., Massachusetts, USA). A gas was input via the second inlet 9 to provide a stream of the first fluid 11 to the microfluidic channel 1 via the aperture 2. Nitrogen gas was employed as the first fluid 11 and was provided by a pressurised cylinder, and the pressure measured using a digital manometer (2023P Digitron, Elektron Technology, Cambridge, UK).

The ultrasound source 3 was driven at 900 mV and with a frequency of from 71-73 kHz to the microfluidic channel 1. The ultrasound source 3 was centred on the section of the microfluidic channel 1 located after the aperture 2. The ultrasound waves generated by the piezoelectric transducer 3 pass through the glass supporting layer 5 to the substrate 4.

At the aperture, bubbles 13 of the gas with a phospholipid interface layer are generated having an average diameter of around 200 μm. As the bubbles 13 travel through the microfluidic channel 1, in the region where the ultrasound source 3 is centred, the ultrasound causes the bubbles 13 to divide into bubbles 13 having an average diameter of around 1.5 μm, and a standard deviation of around 0.8 μm.

Figure 5:
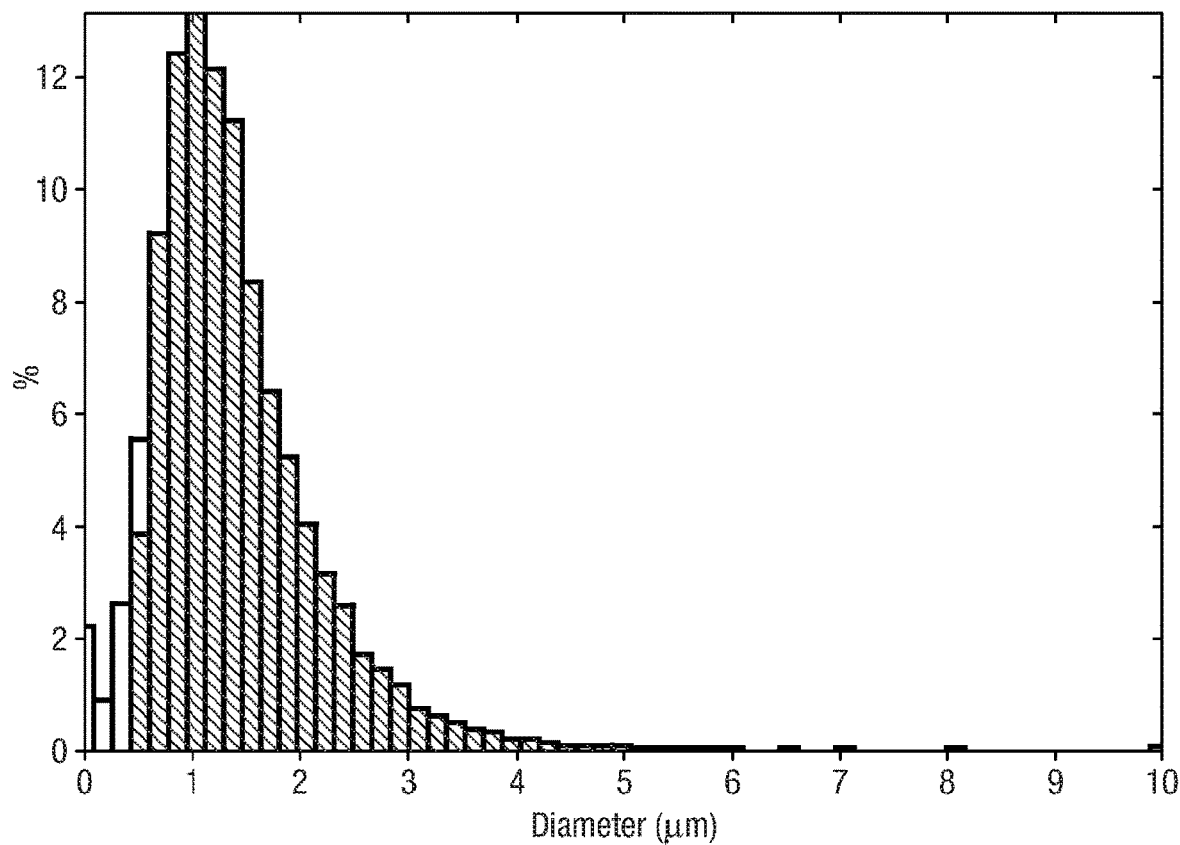
FIG. 5 shows a graph showing bubbles size distribution.

Bubble size, concentration and stability were measured from microscope images acquired using a Leica DM500 microscope (Leica Microsystems GmbH, Wetzlar, Germany) coupled with a CCD camera (MicroPublisher 3.3 RTV, QImaging, Surrey, Canada). Bubble response to ultrasound excitation was determined using a high-throughput co-axial flow focusing apparatus combining optical and acoustic detection. A representative bubble size distribution plot is shown in FIG. 5 (total number of bubbles=11904), showing the absence of larger bubbles typical of conventional batch sonication approaches. The mean bubble diameter is equal to 1.45±0.77 μm, and bubble concentration is equal to $2.17 \times 10^8$ bubbles/mL. Notably, the dimensional properties are comparable to those of lipid-shelled bubbles currently used in the clinic (i.e., SonoVue®). FIGS. 3A and 3B respectively show microscope images of undivided bubbles formed at the aperture 2 and divided bubbles after sonication.

The transition from large to small bubbles is likely to be attributed to either (i) the volumetric oscillation of large bubbles when exposed to low-frequency ultrasound waves within the microfluidic environment (also referred to as cavitation), which may result in bubble collapse or rupture into a smaller bubble population; or (ii) vibrational motion of the air-liquid interface induced by the ultrasound field.

Notably, the duration and magnitude of these phenomena can be controlled by varying the characteristics of both the hydrodynamic and acoustic fields within the device. This will lead to bubbles having different physical properties, and therefore potentially usable for different applications.

Figure 6:
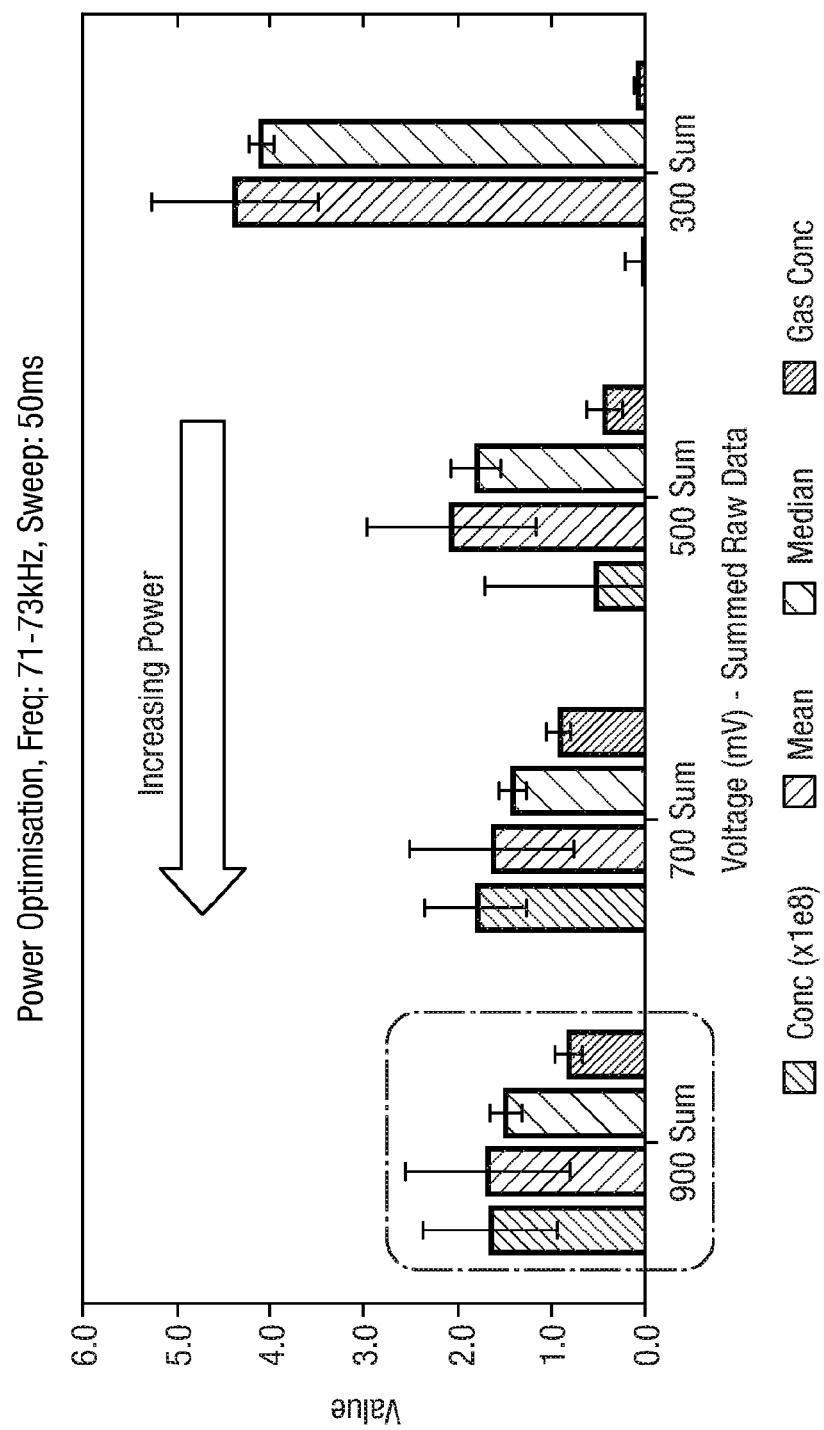
FIG. 6 is a graph showing the dependence of bubble size and concentration on the sonication power (or amplitude of the ultrasound wave) for the exemplary apparatus.

FIG. 6 shows the dependence of bubble size and concentration on the sonication power (or amplitude of the ultrasound wave) for the exemplary apparatus 10. FIG. 6 shows dependence of bubble size (mean and median diameters, in μm) and bubble concentration (bubbles/mL) on the sonication power (ranging from 300 mV to 900 mV). Results show that increasing the excitation power causes a reduction of bubble diameter and an increase in bubble concentration. This allows for controlling on-demand the characteristics of the end-product, and thus its performance as an imaging or therapeutic agent.

FIG. 7 shows dependence of bubble size (Mean and Median diameters, in μm) and bubble concentration (bubbles/mL) on the sonication frequency (ranging from 67 kHz to 73 kHz) for the exemplary apparatus 10. Results show that increasing the excitation frequency results in reduced mean bubbles size and increased concentration, although there appears to be a non-linear dependence between the two. A frequency sweeping sonication regime (in the range 71-73 kHz) was identified as advantageous for obtaining clinically-relevant bubble size and maximising bubble concentration.

TABLE 1

| Operation Principle | Mean Diameter ± SD (μm) | Production Rate (bubbles/sec) |
|---|---|---|
| Microfluidic device | 1.45 ± 0.76 | $2.1 \times 10^6$ |
| Micro-spray (Ref. 1) | 1.7 ± 0.07 | $\sim 1 \times 10^5$ |
| Flow focusing I (Ref. 2) | ~5.0 ± 0.1 | $1 \times 10^6$ |
| Flow focusing II (Ref. 3) | ~5 | $\sim 1.5 \times 10^5$ |
| Sonication-Microfluidics (Ref. 4) | ~10 | NA |
| T-junction (Ref. 5) | ~4.5 | $7.5 \times 10^3$ |

In Table 1 are shown the minimum obtainable mean diameter and maximum production rate for bubbles generated using different microfluidic-based techniques, compared to the method described in the exemplary device of the invention (highlighted). Notably, compared to state-of-the art microfluidic-based technologies (i.e., usually based on flow-focusing or T-Junction architectures), the invention produces bubbles having both clinically-relevant size (i.e., ~1.5 μm mean diameter, compared to 1.58 μm for SonoVue® (Ref 6)) and concentration (i.e., $\sim 2.5 \times 10^8$ bubbles/mL, compared to $\sim 4.1 \times 10^8$ bubbles/mL for SonoVue® (Ref. 6)). The throughput (i.e., number of bubbles generated per unit time) is also higher than conventional microfluidic approaches (i.e., up to $\sim 2 \times 10^6$ bubbles/sec). Compared to other systems our system provides superior performance (in terms of bubble size and concentration) and, importantly, does not require exogenous particles (i.e., cavitation nuclei) which could limit the range of applicable bubble formulations and may compromise the clinical usability of the finished product.

FIG. 8 shows typical radial responses measured using laser scattering at a driving frequency of 3.5 MHz, pulse length of 5 cycles and driving peak negative pressures of 11 kPa and 115 kPa. The expected compression and expansion dominated behaviour is observed, as well as sudden reductions in size at the higher pressure.

Further experimentation was performed according to the following method:

Materials:

The lipids 1,2-distearoyl-sn-glycero-3-phosphocholine (DSPC, 850365), 1,2-dipalmitoyl-sn-glycero-3-phosphocholine (DPPC, 850355), 1,2-distearoyl-sn-glycero-3-phosphoethanolamine-N-[methoxy(polyethylene glycol)-5000] (DSPE-mPEG5000, 880220) and 1,2-dipalmitoyl-sn-glycero-3-phospho-(1'-rac-glycerol) (DPPG, 840455) were purchased as a 25 mg/mL solution in chloroform or powders from Avanti Polar Lipids, Inc. (Alabaster, Ala., USA). Poly(methyl methacrylate) (PMMA) was purchased from theplasticshop.co.uk (Coventry, UK). Epoxy adhesive (Yellow Dual Cartridge) was purchased from RS Components Ltd. (Corby, UK). Nitrogen gas was supplied by the BOC Gases (Guildford, UK). Unless otherwise stated, all other chemicals were purchased from Sigma Aldrich (Gillingham, UK).

Manufacture of Microfluidic Sonication Device:

Initially, the microfluidic architecture was cast in poly (dimethylsiloxane) (PDMS, Sylgard® 184) using a micro-milling replica moulding (µM-REM), technique described previously (REF—FACILE PDMS). Briefly, the architecture, shown in FIG. 3, was micromilled into a PMMA block to form a negative mould. A positive mould was formed by coating the milled PMMA in an 1:1 mixture of epoxy adhesive and curing agent, degassed by vacuum to remove entrapped air bubbles and left to cure at room temperature. After curing, the positive epoxy mould is removed from the PMMA and a 9:1 (w/w) mixture of PDMS and curing agent was poured on top and degassed for 1 hour or more to remove entrapped air bubbles. The PDMS is then cured overnight at room temperature.

To complete the device, the PDMS layer is removed from the positive epoxy mould and the patterned surface activated by plasma treatment (plasma cleaner ATTO, Diener electronic GmbH, Ebhausen, Germany) along with a 180 µm thick, large glass coverslip (TYPE). After about 60-80s of treatment, the PDMS device is pressed firmly against and coverslip and heat treated at 100° C. for 10 minutes.

To create access ports for the nitrogen flow and liquid inlet and outlet, 1/16 inch (1.6 mm) PEEK rods were glued by low cost, solvent free glue (Pritt, Henkel Ltd., Herts., UK) on to the epoxy layer before PDMS pouring. These were removed prior to plasma treatment. After bonding to the glass coverslip, short segments of 3/32 inches (2.4 mm) OD Tygon® tubing (Cole-Parmer Instrument Co. Ltd., London, UK) were inserted into the ports to act as connectors for 1/16 inch (1.6 mm) OD tubing. These were connected to relevant syringes or gas circuits by 18 G blunt needles (Sigma). The PDMS device was then placed on to a custom holder with a 69 kHz frequency, piezoelectric element (0.9 mm×0.9 mm×19.1 mm) mounted underneath and coupled to the device by glycerol. The device channels were flushed with ethanol and the appropriate solvent prior to use.

Production of Lipid Films:

DSPC (25 mg/mL in chloroform) and polyoxyethylene (40) stearate (PEG-405, 10 mg/mL in chloroform) were mixed in a glass vial to form a chloroform solution at a molar ratio of 9:1 respectively. For Definity-like microbubbles, DPPC (25 mg/mL in chloroform), DSPE-mPEG5000 (25 mg/mL in chloroform) and DPPA (1 mg/mL in a chloroform, methanol and water mix were mixed in a glass vial to a 20 mg total of lipid constituents at a molar ratio of 8:1:1 respectively. Chloroform solutions were covered with perforated Parafilm (Bemis Company, Inc., Neenah, Wis., USA) and allowed to evaporate to form a homogenous lipid film.

Resuspension of Lipid Films:

10 mL Milli-Q water (Merck Millipore, Watford, UK) or a water, glycerol and propylene glycol mixture (80:10:10 v/v respectively) was added to the DSPC lipid films or Definity lipid films respectively. The lipids were resuspended into the solvent by stirring at 100° C. on a magnetic stirrer hotplate for a minimum of 30 minutes. The lipids were then homogenously dispersed within the solution by sonication for approximately 2.5 minutes using a micro-sonicator tip fully immersed in the solution at a power setting of 2 to 3 (Microson XL 2000, QSonica, Newtown, Conn., USA).

Production of Lipid Microbubbles by Sonication:

After resuspension and dispersion of lipids into the solvent, the sonicator tip was placed at the air-liquid interface and the headspace in the vial filled with nitrogen gas. The solution was sonicated under constant nitrogen flow for 30 seconds at a power setting of 14 to form a cloudy suspension of microbubbles. The suspension was left to cool to room temperature over 5 minutes. Typically, clinical and research microbubbles use heavy gases, such as perfluorobutane or sulphur hexafluoride, but for comparison to microfluidic sonication derived microbubbles, nitrogen was used.

Production of Lipid Microbubbles by Microfluidic Sonication Device:

The re-suspended, fully dispersed lipid solution was transferred to 10 mL syringe and connected to the liquid inlet port of the microfluidic sonicator device. The gas inlet was connected to a nitrogen cylinder via a dual stage regulator with cutoff valve and an inline electronic pressure mamometer (2023P Digitron, Elektron Technology, Cambridge, UK). A syringe pump (World Precision Instruments Inc., Florida, USA) was used to vary lipid flow rates into the device, whilst gas pressure control was supplied by the regulator. The device was run for a minute to stabilise flow and establish a typical pinch-off bubble regime at the T-junction, indicated by the appearance of a steady stream of large microbubbles (about 200 µm diameter) via the outlet.

To cause breakup of the large microbubbles to the clinically relevant diameter range (about 1-10 µm), an acoustic field was created within the channel by the coupled piezoelectric element. Waveforms were generated by a function generator (Agilent 33220A, Keysight Technologies, Santa Rosa, USA) and amplified via a 55 dB power amplifier (1040L, E&I, Rochester, N.Y., USA). Microbubbles were collected from the outlet tube for examination both before and after the application of sonication for analysis.

Microbubble Concentration, Size and Stability Analysis:

Population statistics—defined here as microbubble concentration, mean diameter and median diameter—were collected using an optical microscopy approach as described in Sennoga et al., 2010 (Ref 6). Briefly, microbubbles produced by sonication were homogenously dispersed by gentle agitation and diluted in Milli-Q water. After further gentle dispersion, 10 µL of diluted microbubbles were loaded on a coverslip-covered haemocytometer. For microbubbles produced by the microfluidic device, the microbubble suspension from the outlet port was directly applied to the haemocytometer for a sample, and covered by a coverslip. Microbubbles were then imaged on brightfield microscope (Leica Microsystems GmbH, Wetzlar, Germany) using a digital camera (MicroPublisher 3.3 RTV, QImaging, Surrey, Canada). A 4× or 40× objective was used for large microbubbles (about 200 µm) and small microbubbles (about 1-10 µm), respectively. Small microbubbles were identified and measured using a custom image processing program in MATLAB (The Mathworks Inc., Natick, Mass., USA), as previously described in Sennoga et al. 2010 (Ref 6), to obtain the desired population statistics. Larger microbubbles used a separate custom image processing script in MATLAB to obtain population statistics.

For stability analysis, population statistics were obtained as described above for 30 minutes. Microbubble samples were loaded onto the haemocytometer and approximately 10 images were captured every 10 minutes on the same sample. From these results, changes in concentration or size were examined. This was repeated three times using a fresh bubble suspension created from a new lipid film each time. Experiments were performed at room temperature (about 18-22° C.).

Figure 16A:
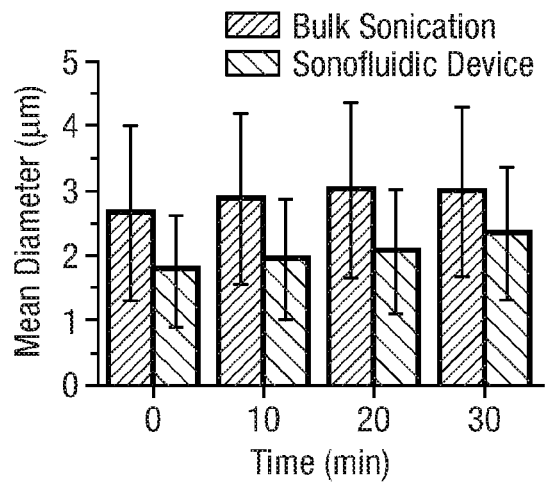
FIG. 16 shows Microbubble stability.
Figure 16B:
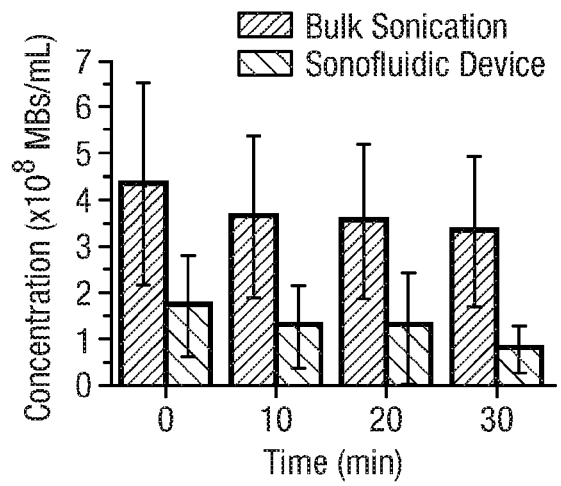

FIG. 16. shows microbubble stability. FIG. 16 shows changes in (a) mean microbubble diameter and (b) concentration of microbubbles produced by the sonofluidic device and bulk sonication over 30 min, measured from bright field microscope images. n=3 per production method.

Optimisation of Microfluidic Sonicator Parameters:

The acoustic parameters of pressure, frequency, and duration of frequency sweep, as controlled by the function generator, were optimised with the criteria of looking for a high number of relatively monodisperse microbubbles at clinically relevant diameters. Additionally, three different concentrations of total lipid per resuspended sample were investigated; 2 mg/mL, 4 mg/mL and 6 mg/mL. A clinically relevant formulation, Definity, was also used to demonstrate the potential of the device.

To optimise the device in terms of highest concentration of microbubbles produced, acoustic parameters of frequency, amplitude, frequency sweep duration were investigated. The frequency of the piezo transducer was initially designed to be about 67 kHz. Frequency optimisation found that higher frequencies resulted in a greater number of microbubbles per mL. Furthermore, a frequency sweep from 71 to 73 kHz was found to be most effective.

Subsequently, a frequency sweep from 71-73 kHz was selected as the optimal acoustic frequency. Power optimisation found increasing pre-amplifier input voltages to a maximum of 900 mV peak to peak, resulted in increasing MB concentrations. Similar results were obtained using either 700 mV vs 900 mV ($1.81 \times 10^8$ vs $1.61 \times 10^8$ MB/mL respectively), however 900 mV was chosen as the optimal setting.

As a frequency sweep was chosen as the optimal frequency setting, sweep duration was also optimised. Interestingly, highest concentrations were found at 1 ms and 1000 ms sweep duration ($1.66 \times 10^8$ vs $2.52 \times 10^8$ MB/mL). 1000 ms sweep duration was chosen as the optimal setting.

Optimal settings on the initial device were chosen to be a 71-73 kHz sweep over 1000 ms, at an input voltage of 900 mV producing $2.52 \pm 0.81 \times 10^8$ MB/mL at a mean diameter of $1.45 \pm 0.76$ μm.

Figure 11:
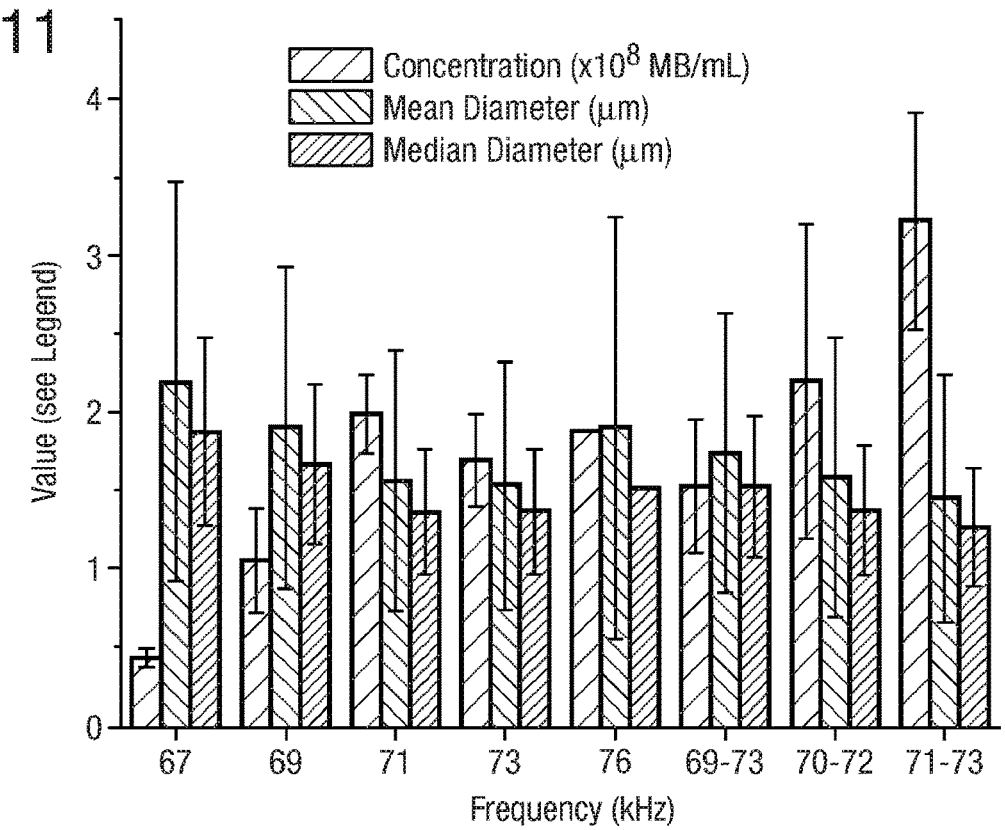
FIG. 11 shows the effect of acoustic frequency on microbubble properties.

FIG. 11 shows the effect of acoustic frequency on microbubble properties. FIG. 11 shows population statistics of microbubbles generated at varying acoustic frequencies. The piezoelectric transducer was run at a pre-amplifier input voltage of 900 mV. The sweeping frequency groups—69-73, 70-72 and 71-73—used a linear frequency sweep over 50 ms. The optimum waveform frequency was chosen as a 71-73 kHz frequency sweep. n=3 per frequency, except 76 kHz which is n=1.

Figure 12:
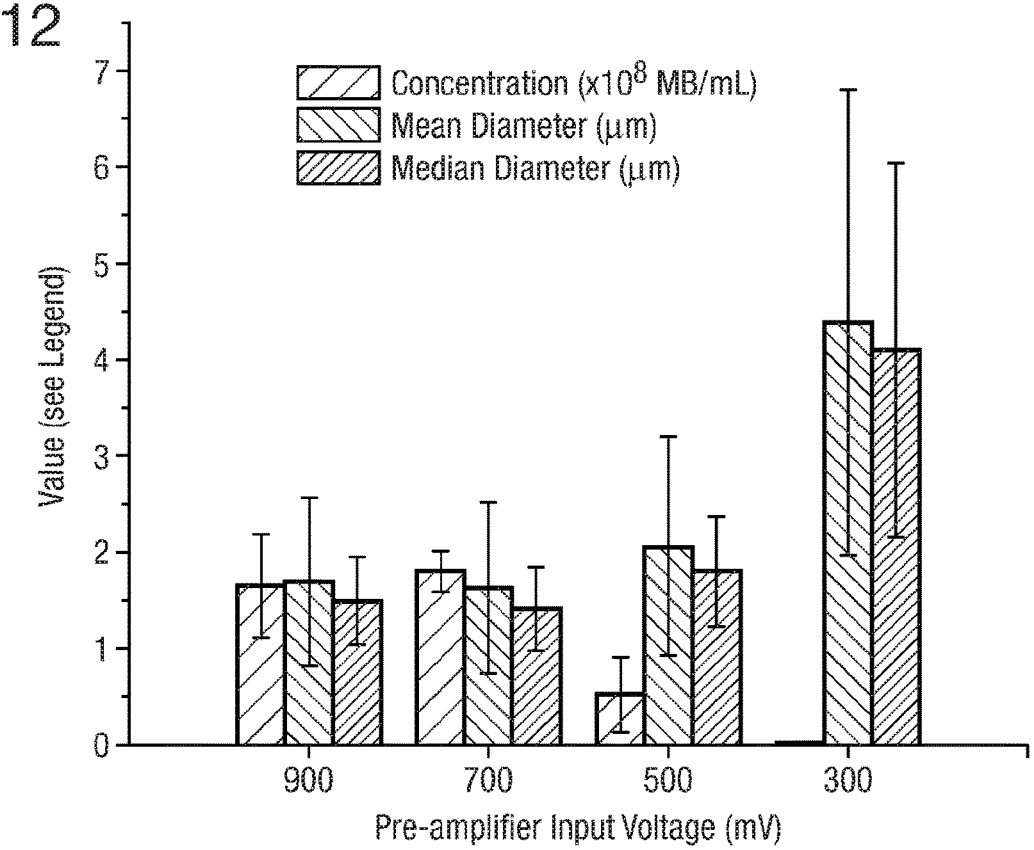
FIG. 12 shows the effect of acoustic power on microbubble properties.

FIG. 12 shows the effect of acoustic power on microbubble properties. FIG. 12 shows population statistics of microbubbles generated at varying acoustic pre-amplifier input voltage. The piezoelectric transducer was run using a frequency sweep of 71-73 kHz over 50 ms. The optimum waveform pre-amplifier input voltage was chosen as 900 mV, although 700 mV was also useable. n=3 per input voltage.

Figure 13:
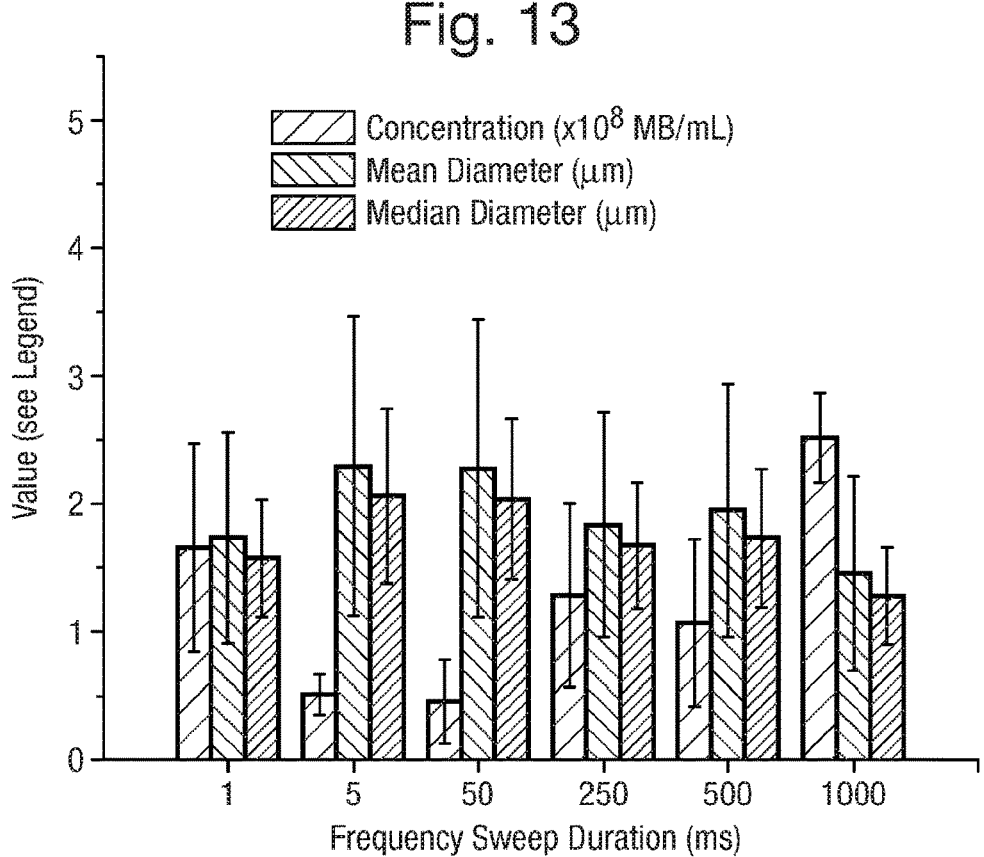
FIG. 13 shows the effect of frequency sweep duration on microbubble properties.

FIG. 13 shows the effect of frequency sweep duration on microbubble properties. FIG. 13 shows population statistics of microbubbles generated at varying acoustic frequency sweep duration. The piezoelectric transducer was run using a frequency sweep of 71-73 kHz at pre-amplifier input voltage of 900 mV. The optimum waveform sweep duration was chosen as 1000 ms. n=3 per frequency sweep, except 50 ms which is n=2.

Impedance Analysis of the Device:

The piezoelectric transducer and complete assembled device filled with air and water was measured for impedance and phase information using a C60 impedance-amplitude-phase analyser (Cypher Instruments, London, UK).

Figure 19:
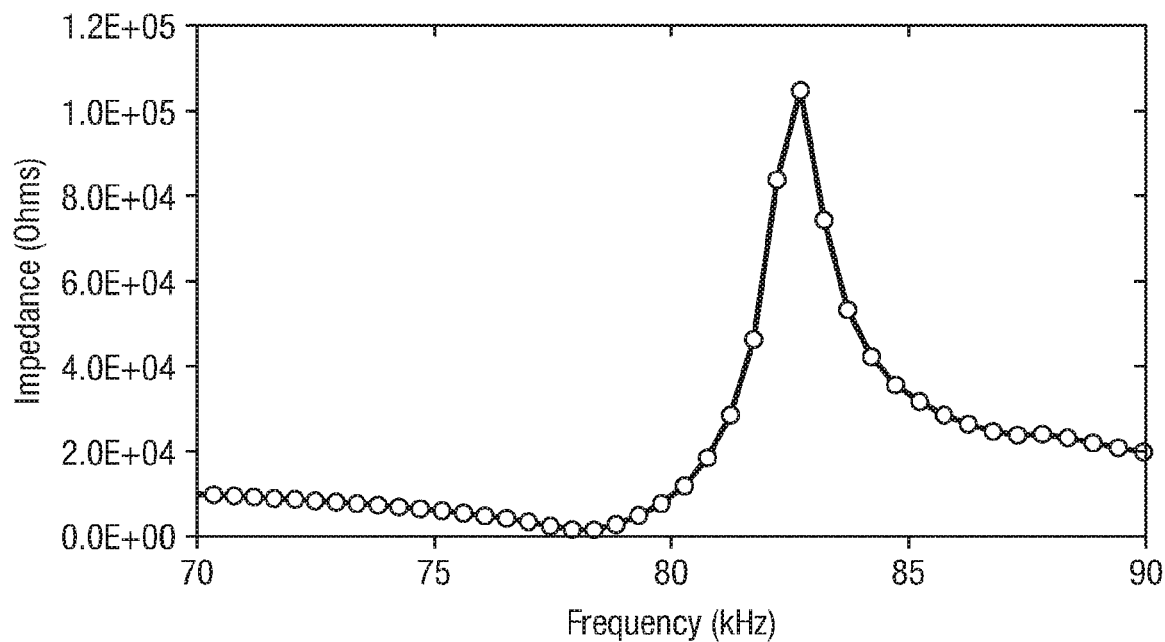
FIG. 19 shows the impedance of current complete device; a peak minimum is found at 78.4 kHz.

FIG. 19 shows the impedance of current of the complete device; a peak minimum is found at 78.4 kHz.

Figure 20:
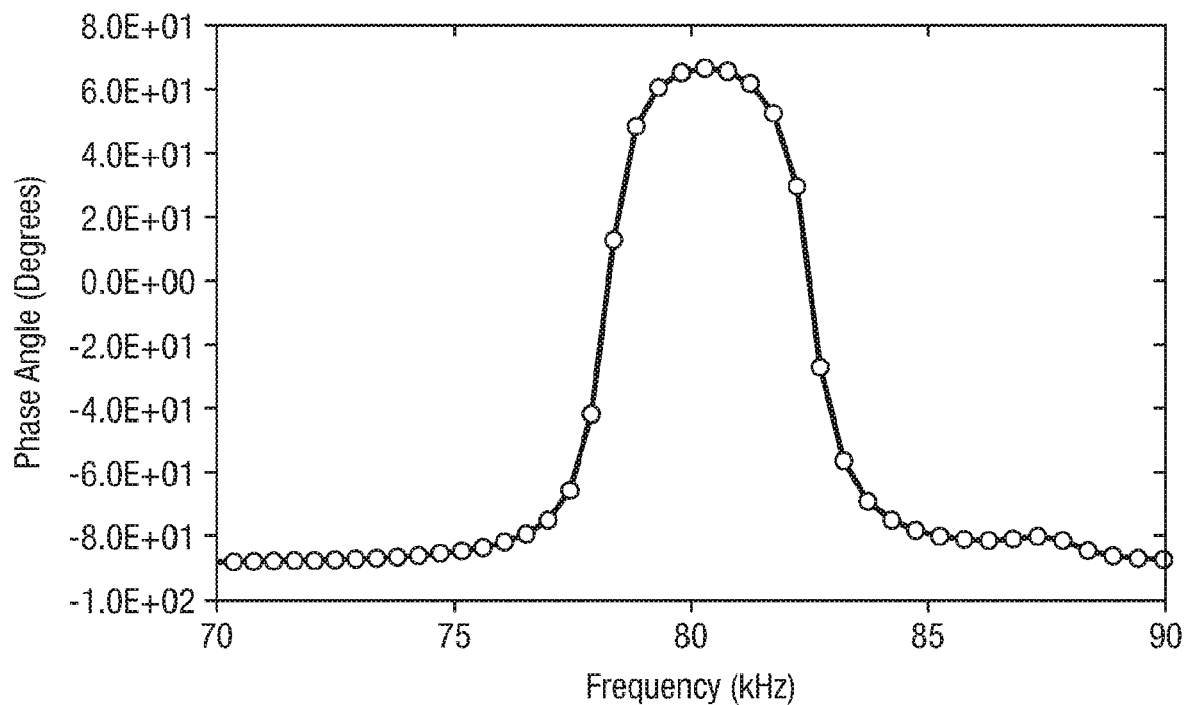
FIG. 20 shows the phase angle of current complete device; a peak maximum is found at 80.3 kHz.

FIG. 20 shows the phase angle of current of the complete device; a peak maximum is found at 80.3 kHz.

Figure 21:
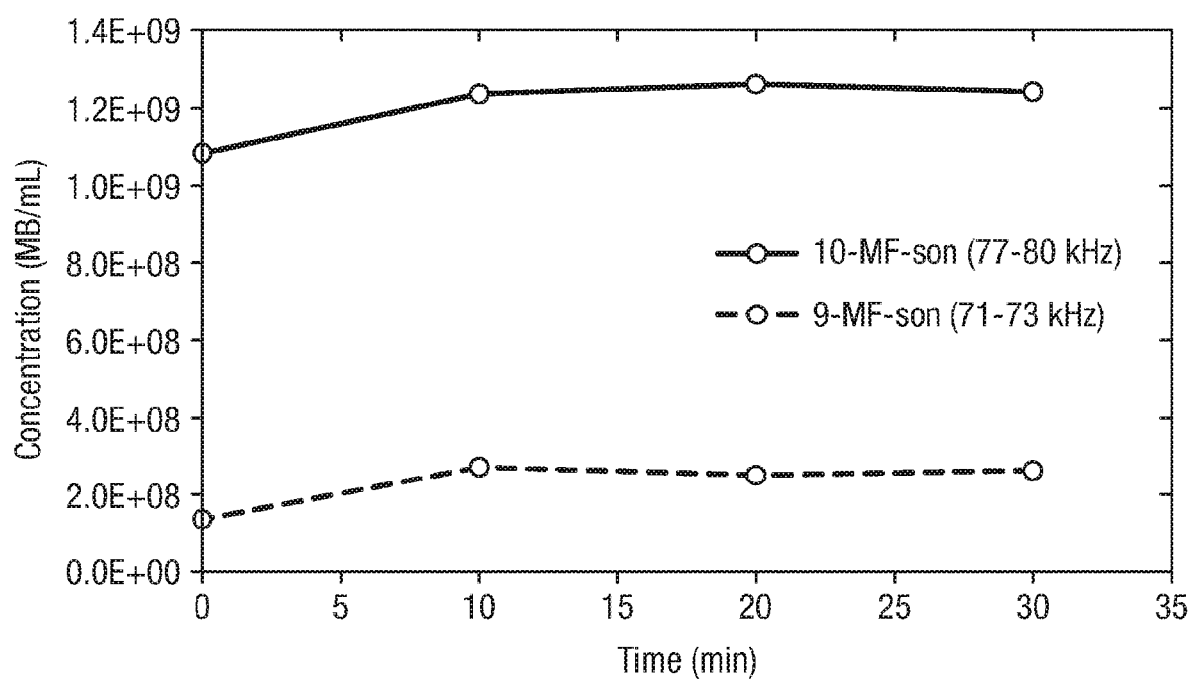
FIG. 21 shows microbubble concentration over time with the device run at original 71-73 kHz (orange) settings and at 77-80 kHz (blue) settings; a higher production of microbubbles is found when the device is run at resonant settings.

FIG. 21 shows microbubble concentration over time with the device run at original 71-73 kHz (orange) settings and at 77-80 kHz (blue) settings; a higher production of microbubbles is found when the device is run at resonant settings.

Single Bubble Acoustic Response:

Microbubble response to ultrasound excitation was instead determined using a high-throughput co-axial flow focusing apparatus combining optical and acoustic detection (REF). Briefly, a laser was co-aligned with a single element acoustic transducer and a photomultiplier tube (PMT) topped with a 40× water immersion objective in a large water tank to reduce acoustic reflections and remove wall effects. A dilute suspension of microbubbles was flowed through a flow focusing microfluidic device such that only single microbubbles would cross through the focal zone. An increase in scattering, as detected by the PMT, triggers the acoustic pulse from the transducer. As the microbubble oscillates in response to the acoustic pressure wave, the cross-sectional scattering area changes, and is detected as a complimentary oscillatory signal by the PMT. By utilising Mie theory, radius-time response curves can be generated for a single microbubbles oscillating in response to an incident acoustic wave. Due to the high sensitivity and sampling rate of the PMT, the acoustic behaviour of free single microbubbles at clinically relevant frequencies (1-10 MHz) can be investigated.

For sonicated microbubbles, samples were diluted and loaded into a syringe attached to the microfluidic device and flow was controlled by syringe pump (WPI Instruments) for single bubble analysis. Due to instabilities in the microfluidic sonicated microbubbles when handled by syringe, the microfluidic sonicator device was instead directly "plumbed" into the microfluidic flow-focusing device on the single bubble acoustic setup, which allowed direct measurement of microbubbles immediately after production.

Figure 15A:
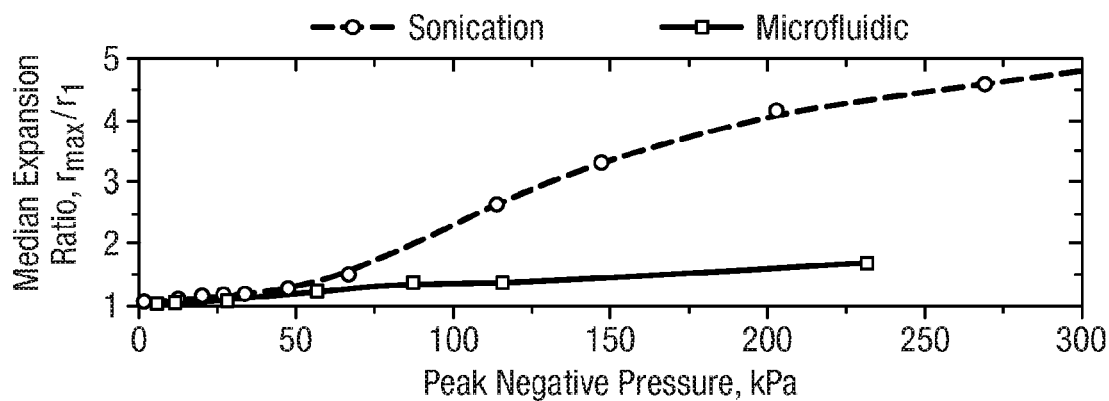
FIG. 15 shows Median microbubble expansion ratio as a function of peak negative driving pressure at 3.5 MHz.
Figure 15B:
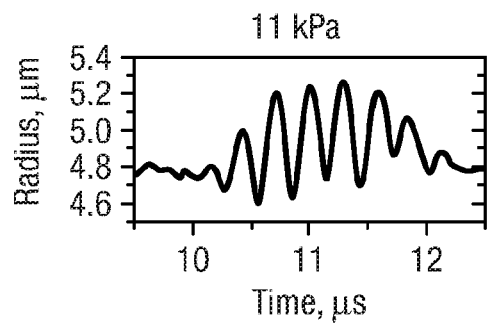
Figure 15C:
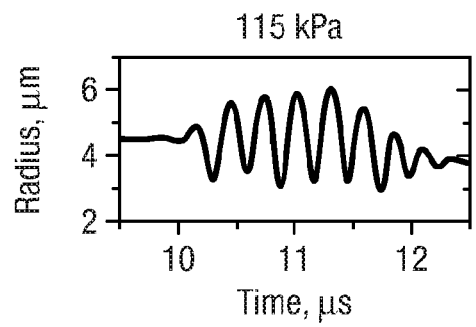

FIG. 15 shows Median microbubble expansion ratio as a function of peak negative driving pressure at 3.5 MHz. Representative radial oscillations of sonofluidic MB at 11 kPa and 115 kPa acoustic pressures are also shown to demonstrate that the microbubble generated by the microfluidic device undergo typical acoustic behaviour.

Modelling:

The pressure field of the transducer was modelled in two dimensions at the channel in COMSOL.

Statistics:

Where applicable, concentrations and mean size were compared using ANOVA.

Results:

Basic Concept:

The microfluidic sonicator device is capable of producing two distinct populations of microbubbles. T-junction microfluidic designs creates bubbles by a pinch off mechanism controlled by hydrodynamic forces, whose diameter is primarily controlled by the aperture dimension, with some variation from gas and liquid flow. In the device architecture presented here, microbubbles of 150-200 μm in diameter are generated with a relatively narrow size distribution (FIG. 9).

Figure 9:
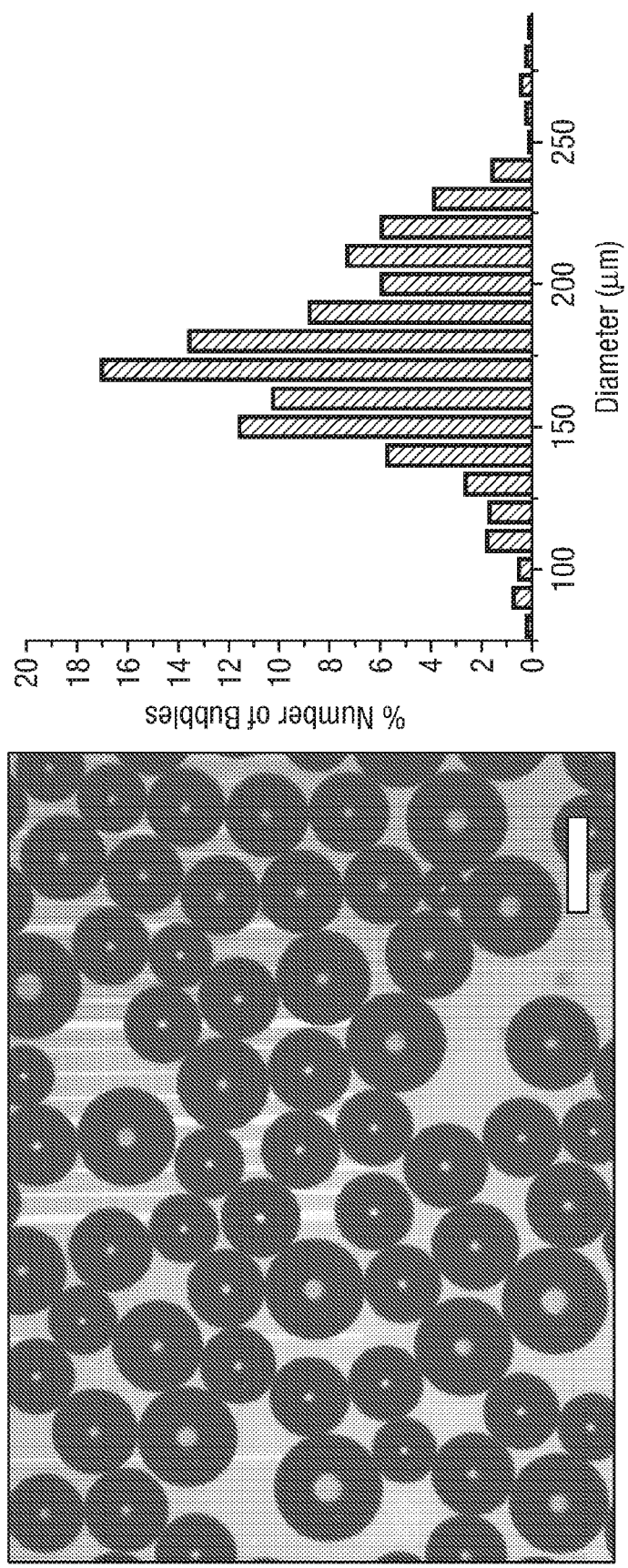
FIG. 9 shows an example 4× brightfield microscopy image and percentage weighted size distribution histogram of bubbles prior to sonication.

FIG. 9 shows an example 4× brightfield microscopy image and percentage weighted size distribution histogram of bubbles prior to sonication. Bubbles are formed from at the T-junction aperture at a size range primarily around 150-200 μm. Histogram data is formed of 20 images and about 1000 bubbles. Scale bar is 200 μm.

After bubble generation via the T-junction, the bubbles pass through the footprint of a piezoelectric transducer. When active, the acoustic waves interact with the large bubbles travelling through the device. Potential mechanisms are described later, but the outcome is the generation of microbubbles below 10 μm in size (FIG. 10).

Figure 10:
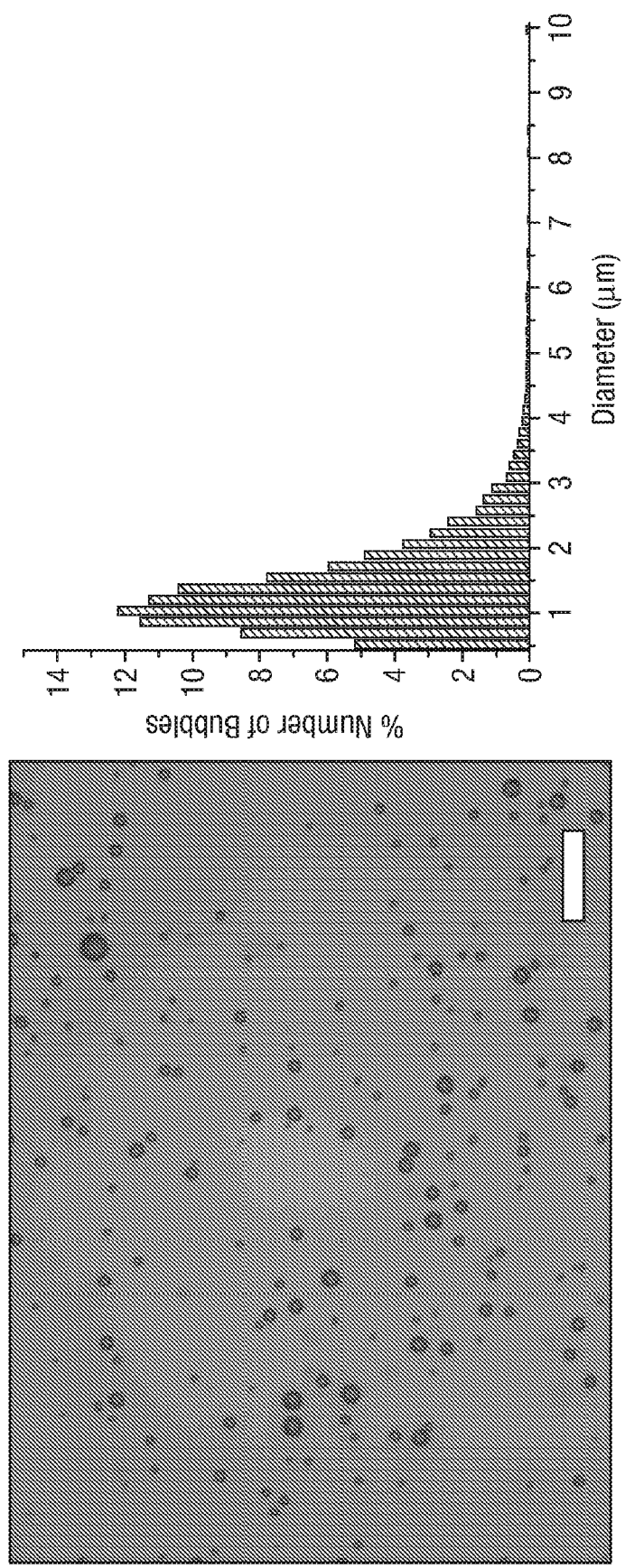
FIG. 10 shows an example 40× brightfield microscopy image and percentage weighted size distribution histogram of bubbles post sonication.

FIG. 10 shows an example 40× brightfield microscopy image and percentage weighted size distribution histogram of bubbles post sonication. Bubbles formed at the T-junction aperture undergo sonication to form microbubbles around 1 μm in diameter. Histogram data is formed of 30 images and about 13000 bubbles. Scale bar is 20 μm. Device reproducibility:

To demonstrate the reproducibility of the design, 3 devices of the same design were constructed and run at the optimal acoustic settings with three 2 mg/mL lipid films.

Three identical devices were constructed and run with the same piezoelectric transducer. (Impedance measurements revealed little difference between the three new devices and the original device, with peak minimum impedance frequencies ranging from about 77-78 kHz.) When run at optimal settings, differences between microbubble outputs were noted, with concentrations ranging from 1.76 to $3.77 \times 10^8$ MB/mL and mean diameters ranging from 2.34 to 2.92 μm. It was noted, that although the three devices had the same architecture, manual methods of construction led to changes in the exact positioning of the chip on the glass substrate, which in turn led to changes in the arrangement of the channels on the transducer.

Figure 18:
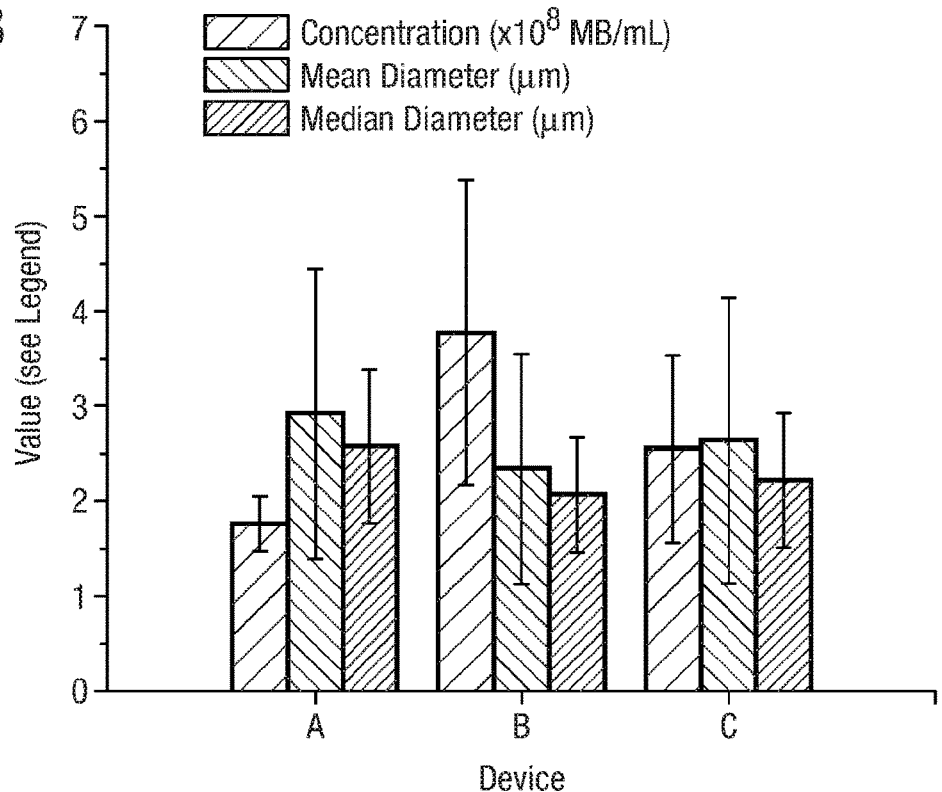
FIG. 18 shows the reproducibility of device manufacture.

FIG. 18 shows the reproducibility of device manufacture. FIG. 18. shows population statistics of microbubbles generated at a frequency sweep from 71-73 kHz over 1000 ms at a pre-amplifier input voltage of 900 mV using a 2 mg/mL DSPC:PEG40S film on three different devices. n=3 per device.

Comparison to microbubbles produced by standard sonication:

DSPC:PEG40S (9:1) microbubbles were prepared by sonication and by the microfluidic sonication device and monitored over 30 minutes after production for static, environmental stability. Sonication produced a greater number of microbubbles ($4.34 \times 10^8$ vs $1.71 \times 10^8$ MB/mL) with a larger mean diameter (2.65 vs 1.75 μm). Additionally, microbubbles produced by microfluidic sonication exhibited a much tighter size distribution around the mean diameter, with few microbubbles greater than 4 μm (FIG. 14).

Figure 14:
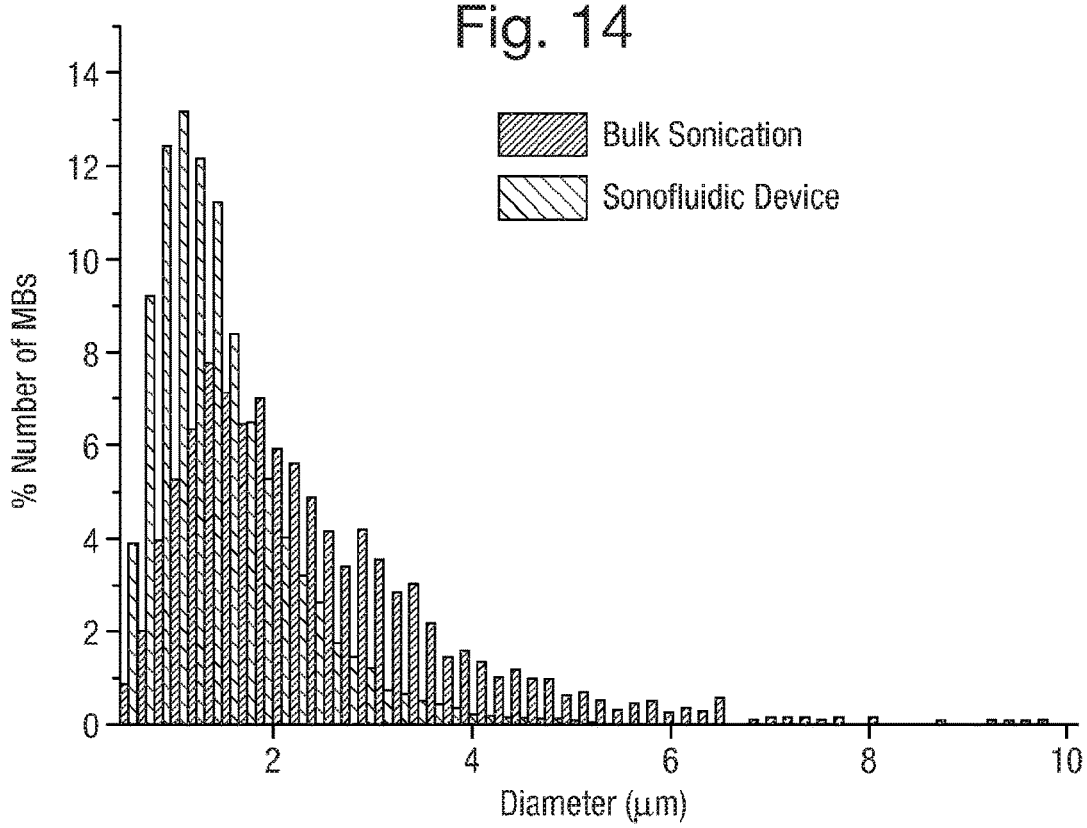
FIG. 14 shows percentage-weighted, size distribution histogram of microbubbles (MBs) produced by the sonofluidic device and bulk sonication using a 2 mg/mL DSPC: PEG40S film. n=3 per production method.

FIG. 14 shows percentage-weighted, size distribution histogram of microbubbles (MBs) produced by the sonofluidic device and bulk sonication using a 2 mg/mL DSPC:PEG40S film. n=3 per production method.

Over 30 minutes, both types of microbubbles underwent a gradual decrease in concentration and increase in size. By 30 minutes, the number of microbubbles produced by the microfluidic sonication device had decreased by 50%, whereas microbubbles produced by standard sonication had decreased by about 25%.

Single bubble acoustic response was also investigated. Microbubble acoustic response significantly differed depending upon production method, with microbubbles produced by the microfluidic sonication device exhibiting lower expansion ratios over increasing acoustic pressures.

Modification of Formulation:

Total lipid concentration of the DSPC:PEG40S microbubbles were varied to determine the effect on microbubble production. It was found that increasing the lipid concentration from 2 to 6 mg/mL increased resultant microbubble concentration from $4.5 \times 10^7$ to $2.12 \times 10^8$ under optimal acoustic conditions. There was less of an increase from 4 to 6 mg/mL ($1.78 \times 10^8$ vs $2.12 \times 10^8$ MB/mL).

A "Definity" like formulation was also tested in the microfluidic sonication device using 2 mg/mL total lipid concentration. Unlike the DSPC:PEG40S microbubbles, the resuspension solvent is a water:glycerol:propylene glycol solution. The microbubble concentration using "Definity" was significantly higher than the DSPC:PEG40S, at $7.79 \times 10^8$ MB/mL.

Figure 17:
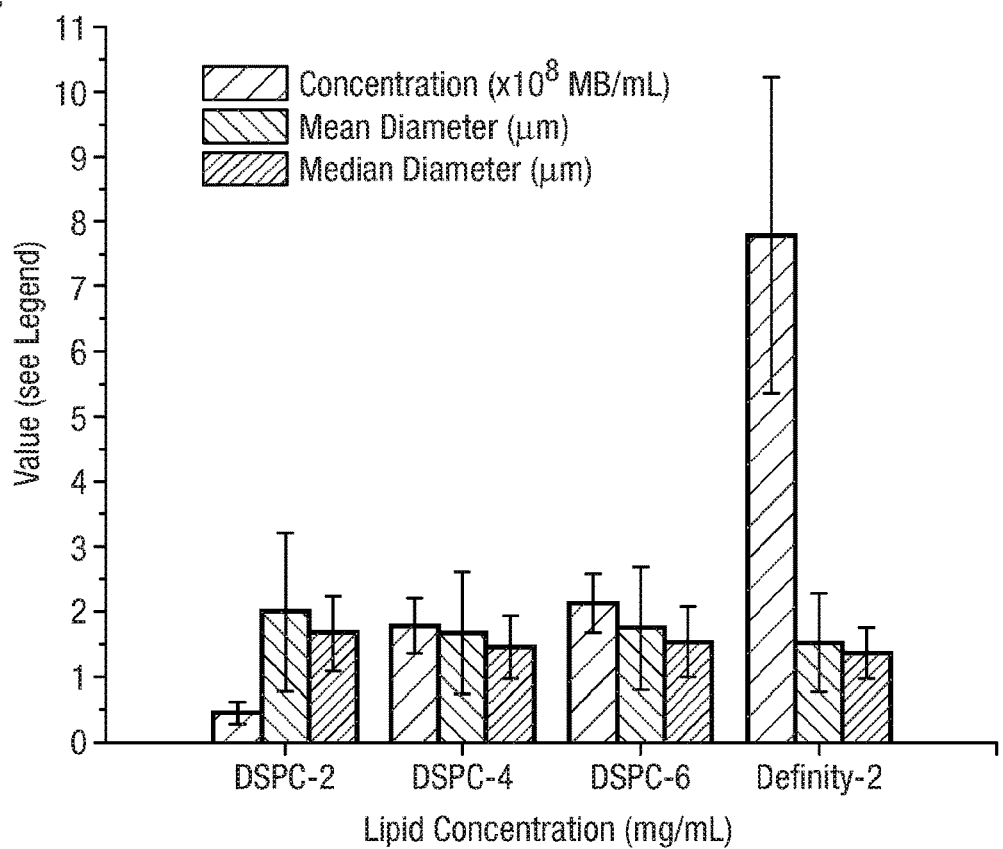
FIG. 17 shows the effect of total lipid concentration and formulation on microbubble properties.

FIG. 17 shows the effect of total lipid concentration and formulation on microbubble properties. FIG. 17. Shows population statistics of microbubbles generated at a frequency sweep from 71-73 kHz over 1000 ms at a pre-amplifier input voltage of 900 mV at different lipid concentrations of DSPC:PEG40S and a Definity like formulation. Optimisation of lipid concentration and formulation can improve microbubble production. n=3 per formulation. The microfluidic channel of invention provides tight control over bubble size and material content, but an ultrasound transducer is integrated into the device to initiate bubble formation and promote adsorption of surfactant on to the bubble surface (in conventional devices this is achieved by the high shear rates generated at narrow orifice). This enables larger channel dimensions to be used than in current state-of-the-art devices and provides control over surface properties. Thus:

The invention is able to produce bubbles having both clinically-relevant size (i.e., ~1.5 μm mean diameter) with higher throughput (i.e., number of bubbles generated per unit time) than conventional microfluidic approaches (i.e., up to ~$2 \times 10^6$ bubbles/sec).

The device lifetime is significantly increased compared to state-of-the-art microfluidic approaches as the larger channels reduce the risk of clogging.

The usability of the device is significantly improved, particularly in terms of easiness of device priming, cleaning and interfacing with pumping units. This is of particular importance for industrial applications.

Bubbles can be produced without the need for any viscosity agent additives (e.g., glycerol) of nucleation agents which are commonly used in conventional microfluidic-based production methods to facilitate bubble formation but which reduce production rates and are potential contaminants.

Compared to conventional bulk sonication methods, the invention offers the advantage of higher control over the properties of the physical environment in which bubble formation occurs, allowing for improved reproducibility between experiments and narrower bubble size distribution.

Furthermore, contrary to bulk sonication, the sonication parameters of the invention can be finely adjusted in order to optimise the characteristics of the finished product, such as bubble size, size distribution and concentration, and physical properties of the bubble interface layer (i.e., degree of lipid packing and viscosity) which are important for bubble stability and response to ultrasound.

Variations of the above described embodiments are possible in light of the above teachings. It is to be understood that the invention may be practised otherwise than specifically described herein without departing from the scope of the invention as defined by the appended claims.

REFERENCES

Ref 1: S. A. Peyman, R. H. Abou-Saleh, J. R. McLaughlan, N. Ingram, B. R. Johnson, K. Critchley, S. Freear, J. A. Evans, A. F. Markham, P. L. Coletta, Expanding 3D geometry for enhanced on-chip microbubble production and single step formation of liposome modified microbubbles, Lab on a Chip, 12 (2012) 4544-4552.

Ref 2: K. Hettiarachchi, E. Talu, M. L. Longo, P. A. Dayton, A. P. Lee, On-chip generation of microbubbles as a practical technology for manufacturing contrast agents for ultrasonic imaging, Lab Chip, 7 (2007) 463-468.

Ref 3: E. Castro-Hernandez, W. van Hoeve, D. Lohse, J. M. Gordillo, Microbubble generation in a co-flow device operated in a new regime, Lab on a Chip, 11 (2011) 2023-2029.

Ref 4: H. Chen, J. Li, W. Zhou, E. G. Pelan, S. D. Stoyanov, L. N. Arnaudov, H. A. Stone, Sonication—Microfluidics for Fabrication of Nanoparticle-Stabilized Microbubbles, Langmuir, 30 (2014) 4262-4266.

Ref 5: C. Chen, Y. Zhu, P. W. Leech, R. Manasseh, Production of monodispersed micron-sized bubbles at high rates in a microfluidic device, Applied Physics Letters, 95 (2009) 144101.

Ref 6: C. A. Sennoga, V. Mahue, J. Loughran, J. Casey, J. M. Seddon, M. Tang, R. J. Eckersley, On sizing and counting of microbubbles using optical microscopy, Ultrasound in medicine & biology, 36 (2010) 2093-2096.

The invention claimed is:

1. The method of generating bubbles of a first fluid in a second fluid, the method comprising:
    flowing a stream of the second fluid through a microfluidic channel;
    injecting a stream of the first fluid into the microfluidic channel through an aperture such that bubbles of the first fluid form in the second fluid; and
    sonicating the microfluidic channel with ultrasound using an ultrasound source so as to cause the bubbles formed at the aperture to divide;
    wherein the ultrasound has a frequency corresponding to a resonance of the microfluidic channel.

2. A method according to claim 1, wherein the sonication is applied to the microfluidic channel at a location adjacent to the aperture.

3. A method according to claim 1, wherein the sonication is applied to a length of the microfluidic channel of at least 10 mm and/or to a length of the microfluidic channel of at most 100 mm.

4. A method according to claim 1, wherein the ultrasound has a frequency of at least 20 kHz.

5. A method according to claim 1, further comprising:
    measuring the impedance and/or phase angle of the ultrasound source sonicating the microfluidic channel;
    wherein the frequency corresponding to a resonance of the microfluidic channel is determined based on measuring impedance and/or phase angle.

6. A method according to claim 1, wherein the microfluidic channel has a hydraulic diameter of 1 mm or less.

7. A method according to claim 1, wherein the undivided bubbles formed at the aperture have an average diameter of at least 100 μm.

8. A method according to claim 1, wherein the divided bubbles after sonication have an average diameter of at most 10 μm and/or the diameters of the divided bubbles after sonication have a coefficient of variation of less than 60%.

9. A method according to claim 1, wherein the second fluid is a liquid.

10. A method according to claim 9, wherein the second fluid is an aqueous solution.

11. A method according to claim 1, wherein the first fluid is a gas or a liquid.

12. A method according to claim 1, wherein the step of injecting the first fluid into the microfluidic channel is performed in the presence of a surfactant such that the bubbles formed at the aperture comprise the surfactant at an interface with the second fluid.

13. A method according to claim 12, wherein the stream of the second fluid further comprises the surfactant.

14. A method according to claim 12, wherein the surfactant comprises a phospholipid, a protein or a polymer.

15. A method according to claim 12, wherein the surfactant and/or the first fluid comprises a pharmaceutical product.

* * * * *